(12) United States Patent
Perlin

(10) Patent No.: US 8,696,649 B2
(45) Date of Patent: Apr. 15, 2014

(54) LAPAROSCOPIC SURGICAL INSTRUMENT HAVING ROTATABLE HANDLES WITH A COUPLER FEATURE

(75) Inventor: Alfred Perlin, Highland Park, IL (US)

(73) Assignee: Marsh Surgical, Inc., Glencoe, IL (US)

( * ) Notice: Subject to any disclaimer, the term of this patent is extended or adjusted under 35 U.S.C. 154(b) by 1511 days.

(21) Appl. No.: 11/349,757

(22) Filed: Feb. 7, 2006

(65) Prior Publication Data

US 2006/0287640 A1    Dec. 21, 2006

Related U.S. Application Data

(60) Provisional application No. 60/690,968, filed on Jun. 16, 2005, provisional application No. 60/711,347, filed on Aug. 25, 2005.

(51) Int. Cl.
*A61B 17/00*    (2006.01)

(52) U.S. Cl.
USPC .............................................. 606/1; 606/205

(58) Field of Classification Search
USPC ................... 606/1, 205, 208, 167, 170, 174; 600/266, 562, 564, 118, 131, 137, 141, 600/142, 146
See application file for complete search history.

(56) References Cited

U.S. PATENT DOCUMENTS

| | | | |
|---|---|---|---|
| 2,113,246 A | 4/1938 | Wappler | |
| 4,084,594 A | 4/1978 | Mosior | |
| 5,603,723 A * | 2/1997 | Aranyi et al. | 606/205 |
| 5,954,731 A * | 9/1999 | Yoon | 606/144 |

FOREIGN PATENT DOCUMENTS

| | | |
|---|---|---|
| DE | 94 01 042 | 3/1994 |
| DE | 91 17 265 | 11/1998 |
| WO | WO 96/04856 | 2/1996 |

OTHER PUBLICATIONS

Communication Relating to the Results of the Partial International Search for International Application No. PCT/US2006/022548, mailed Oct. 25, 2006 (6 pages).

* cited by examiner

*Primary Examiner* — Thomas McEvoy
*Assistant Examiner* — Sarah W Aleman
(74) *Attorney, Agent, or Firm* — Law Office of Marc D. Machtinger, Ltd.

(57) ABSTRACT

A laparoscopic instrument including a pair of handles pivotally rotatable among at least two lockable positions. The instrument includes two drums attached to respective ones of the handles, a tool drum coupled to one of the drums, and a shaft passing through apertures formed in each of the drums and the tool drum. The drums are rotatable around the shaft to cause the handles to be rotated among the lockable positions. The shaft includes a pair of winglets disposed along a length of the shaft. A push-button is connected to an end of the shaft to slide the shaft relative to the three drums. When the push-button is depressed, the winglets lock the handles together, allowing them to freely rotate about the shaft. When the push-button is released, pins secure one of the drums to a housing to allow rotation of one of the handles relative to the other.

9 Claims, 22 Drawing Sheets

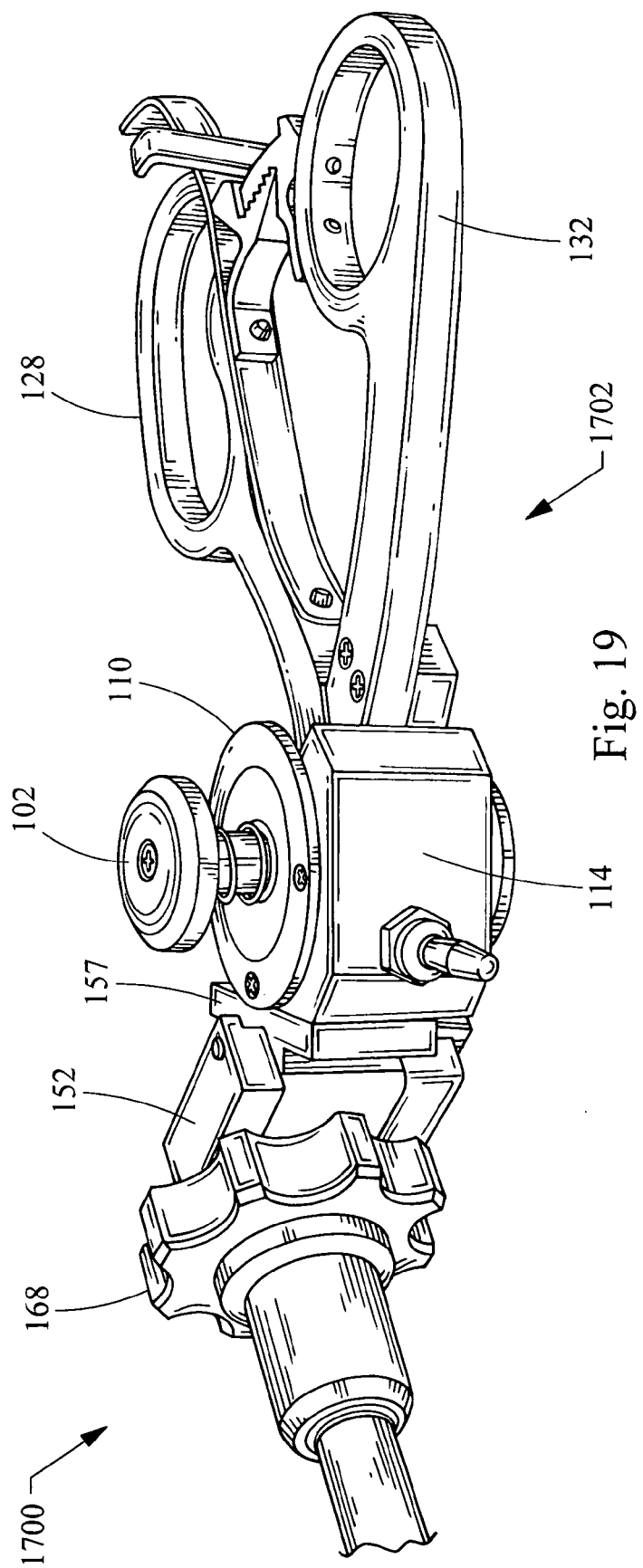

LAPAROSCOPIC SURGICAL INSTRUMENT HAVING ROTATABLE HANDLES WITH A COUPLER FEATURE

RELATED APPLICATIONS

This application claims priority to U.S. Provisional Patent Application Ser. No. 60/690,968 filed Jun. 16, 2005, titled "Laparoscopic Tool Coupler," and U.S. Provisional Patent Application Ser. No. 60/711,347 filed Aug. 25, 2005, titled "Laparoscope's Tool With In Situ Tool Exchange," each of which is incorporated herein in its entirety.

FIELD OF THE INVENTION

The present invention relates generally to laparoscopic instruments and, more particularly, to a laparoscopic instrument having rotatable handles with a coupler feature.

BACKGROUND OF THE INVENTION

Laparoscopic instruments are used during laparoscopy procedures, which are generally used to examine a patient and/or to perform minor surgery on the patient. For example, a laparoscopic instrument can be used to examine the patient's abdominal cavity for signs of disease or abnormality. In addition, fully invasive surgery may be avoided by using the laparoscopic instrument to perform relatively minor surgery. Similarly, in minimally invasive arthroscopic procedures, such as on a knee joint, an arthroscopic instrument is used to access joints or bones.

The laparoscopic (or arthroscopic) instrument generally includes a grasping end and an operating end that are connected by a flexible hollow cylindrical shaft. The laparoscopic instrument is introduced into the patient through a cannula/trocar unit. After the laparoscopic instrument is inserted into the patient through a cannula that is anchored to the body via a small incision, the surgeon may insert one of a plurality of laparoscopic tools into the laparoscopic instrument to perform a particular surgical procedure. For example, if a grasping procedure is required the surgeon will insert a grasping tool in the laparoscopic instrument. Similarly, if a cutting procedure is required the surgeon will insert a cutting tool in the laparoscopic instrument.

One problem associated with current laparoscopic instruments is that they may cause the surgeon to lose his or her "feel" when changing laparoscopic tools. During surgery, the surgeon develops a particular "feel" associated with the location and positioning of the laparoscopic instrument relative to the patient's internal cavities. Because the surgeon may be required to perform several procedures during a single surgery, each procedure requiring a different laparoscopic tool, the surgeon may lose the "feel" when changing the laparoscopic tools.

In one exemplary scenario, the surgeon uses an examination tool to find the best location for performing a cutting procedure. After finding the best location, the surgeon retrieves the laparoscopic instrument from within the patient, replaces the examination tool with a cutting tool, and reinserts the laparoscopic instrument inside the patient. It can be time consuming and frustrating for the surgeon to locate, for a second time, the best location for performing the cutting procedure.

Another problem associated with current laparoscopic instruments is that they have a fixed grasping end and, therefore, limit the ability and/or comfort of the surgeon in attaining desired positions within the patient's body. Depending on the surgical procedure, the surgeon must often change the position of the laparoscopic instrument or contort his or her body position to reach various parts of a patient's internal cavity. For example, the surgeon will often attempt to achieve the best cutting position before performing a delicate cutting procedure by rotating and/or moving the grasping end of the laparoscopic tool at various uncomfortable and awkward positions. Because the grasping end of the laparoscopic instrument is fixed, the surgeon must perform the cutting procedure by grasping the laparoscopic tool at an uncomfortable or awkward position that decreases the likelihood of a successful surgical procedure, or must contort his or her body to access a hard-to-reach area of the patient's internal cavity.

Yet another problem associated with current laparoscopic instruments is that the surgeon must clasp the operating end together in order to hold a grasping tool in a closed position. Prolonged clasping results in hand fatigue and also undesirably ties up one of the surgeon's hands to perform other tasks. If the surgeon removes or relaxes his hand from the grasping end, then the grasping tool may lose its grip on the internal body structure it was grasping.

Thus, there is a need to provide a laparoscopic tool that allows the surgeon to retain the "feel" developed during a surgical procedure by changing laparoscopic tools without having to remove the laparoscopic instrument from within the patient's body. There is also a need for an adjustable grasping end for a laparoscopic or arthroscopic instrument for attaining desired and/or comfortable operating positions. There is yet another need for a laparoscopic or arthroscopic instrument that can lock a grasping tool in a fixed position without requiring manual clasping by the surgeon. The present invention fulfills these and other needs.

SUMMARY OF THE INVENTION

In an aspect of the present invention, a laparoscopic instrument includes a first handle pivotally rotatable among at least two lockable positions, or, in another aspect of the present invention, among at least three lockable positions. The instrument may further include a drum attached to the first handle and a shaft passing through the drum. The drum is rotatable around the shaft to cause the first handle to the pivotally rotated among the at least two lockable positions. The instrument includes a second handle pivotally rotatable among the at least two or three lockable positions with the first handle. The instrument may further include a second drum attached to the second handle. The shaft also passes through the second drum, which is rotated around the shaft to cause the second handle to be pivotally rotated among the at least two or three lockable positions. The instrument may further include a drum attached to the first handle, a second handled attached to a second drum, a tool drum coupled to the drum and the second drum, and a shaft passing through all three drums so as to be rotatable among the at least two or three lockable positions. The shaft may further include winglets disposed along a length of the shaft and positioned to lock together any combination pair of the drum, the second drum, and the tool drum while the shaft is rotated among the at least two or three lockable positions. The instrument may still further include a housing, a drum attached to the handle, a shaft passing through the drum for securing the drum along a central axis of the housing and a push-button connected to the shaft for moving the shaft between one of the at least two lockable positions and another position. The instrument may further include a tool drum connected to the handle and a tool having a ball end and a tool end. The ball end of the tool is removably connected to the tool drum in any of the at least two or three lockable positions.

In still another aspect of the present invention, a laparoscopic instrument has a transverse axis along which a tip is disposed. The laparoscopic instrument includes a trigger handle pivotally rotatable among at least two lockable positions about an axis orthogonal to the transverse axis. The instrument may further include a trigger drum attached to the trigger handle, a tool drum rotationally secured to the trigger drum in the at least two lockable positions, and a fixing drum attached to a fixing handle. The fixing drum is rotationally secured to the trigger drum when the trigger drum is in an unlocked position. The instrument further includes a winged shaft for axially securing the trigger drum, the tool drum, and the fixing drum to each other. The winged shaft can include one or more winglets, spline parts, keys, or pins. The winged shaft is movable between a first position and a second position. The tool drum and the trigger drum are rotationally secured with respect to each other in the first position, and the trigger drum and the fixing drum are rotationally secured with respect to each other in the second position. The first position corresponds to one of the at least two lockable positions.

In yet another aspect of the present invention, a method of using a laparoscopic instrument has a trigger drum connected to a handle of the instrument. The method includes rotating the trigger drum from a first drum locked position to a second drum locked position. The method may further include unlocking the trigger drum from the first drum locked position before rotating the drum to the second drum locked position. The rotating may include rotating the trigger drum together with a fixing drum to a second drum position. The method may further include depressing a push-button to unlock the trigger drum from the first drum locked position and releasing the push-button to lock the trigger drum and the fixing drum in the second drum locked position. The method may further include disengaging the fixing drum from at least one push pin when depressing the push-button. The method may further include positioning a shaft in a first shaft position to rotationally secure the trigger drum to the tool drum in the first drum locked position, urging the shaft from the first shaft position to a second shaft position to rotationally secure the trigger drum to the fixing drum in an unlocked drum position, the trigger drum being rotationally released from the tool drum in the unlocked drum position, rotating the fixing drum together with the trigger drum to the second drum position, and urging the shaft from the second shaft position to the first shaft position to rotationally secure the trigger drum to the tool drum in the second drum locked position. The method may further include inserting a tool into the laparoscopic instrument and linearly displacing the tool to manipulate a tool device located at an end of the tool. The linearly displacement may be carried out by rotating a handle that is coupled to the trigger drum.

The above summary of the present invention is not intended to represent each embodiment, or every aspect, of the present invention. Additional features and benefits of the present invention are apparent from the detailed description, figures, and claims set forth below.

BRIEF DESCRIPTION OF THE FIGURES

FIG. 1AI is a perspective bottom view of the tool drum shown in FIG. 1A according to an embodiment of the present invention.

FIG. 19 is a perspective view of the shotgun subassembly of FIG. 17 showing an assembled shotgun subassembly in an open breech position.

Figure 1A:
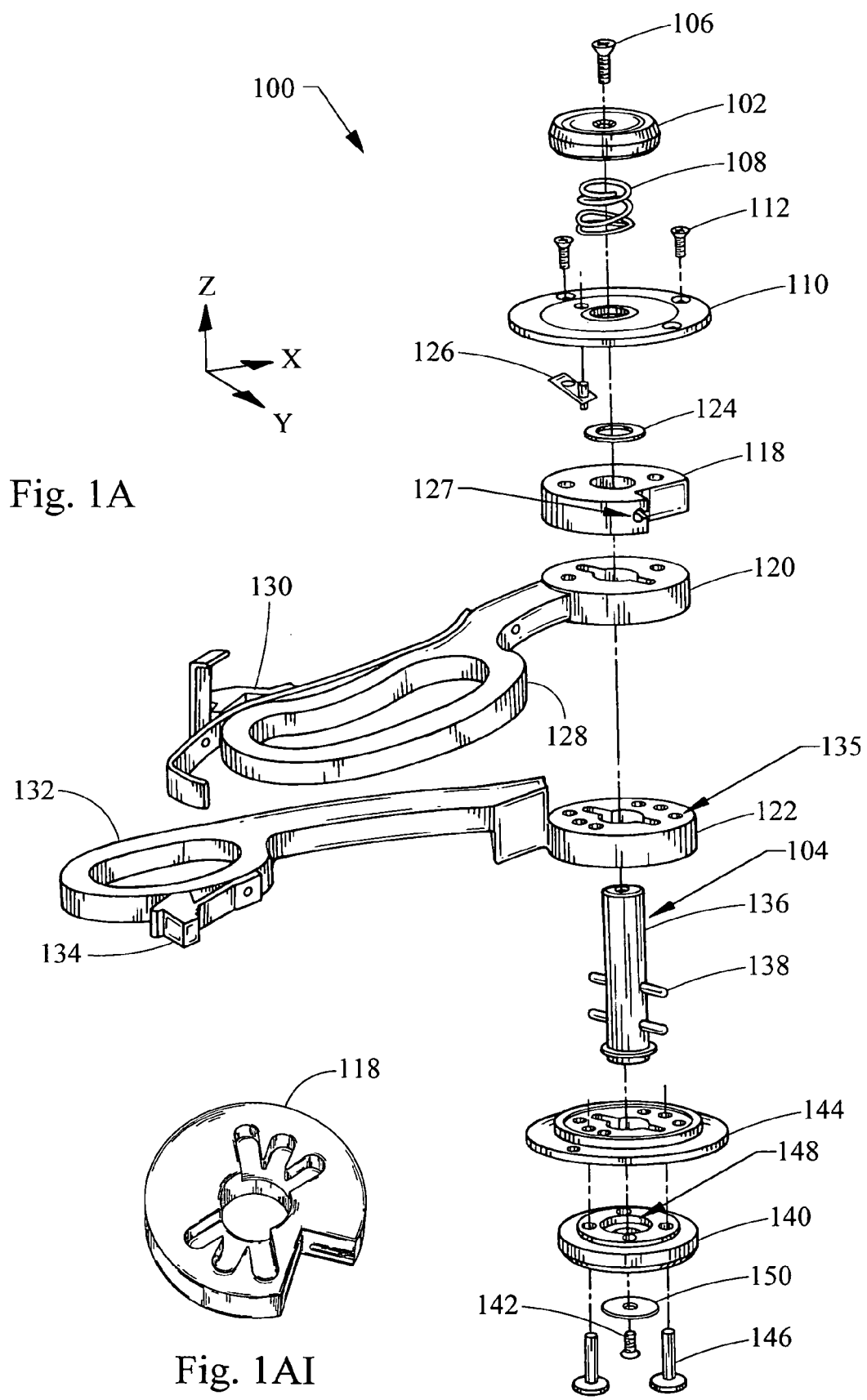
FIG. 1A is an exploded perspective view showing a first portion of a laparoscopic instrument according to one embodiment of the present invention.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE ILLUSTRATED EMBODIMENTS

Figure 1B:
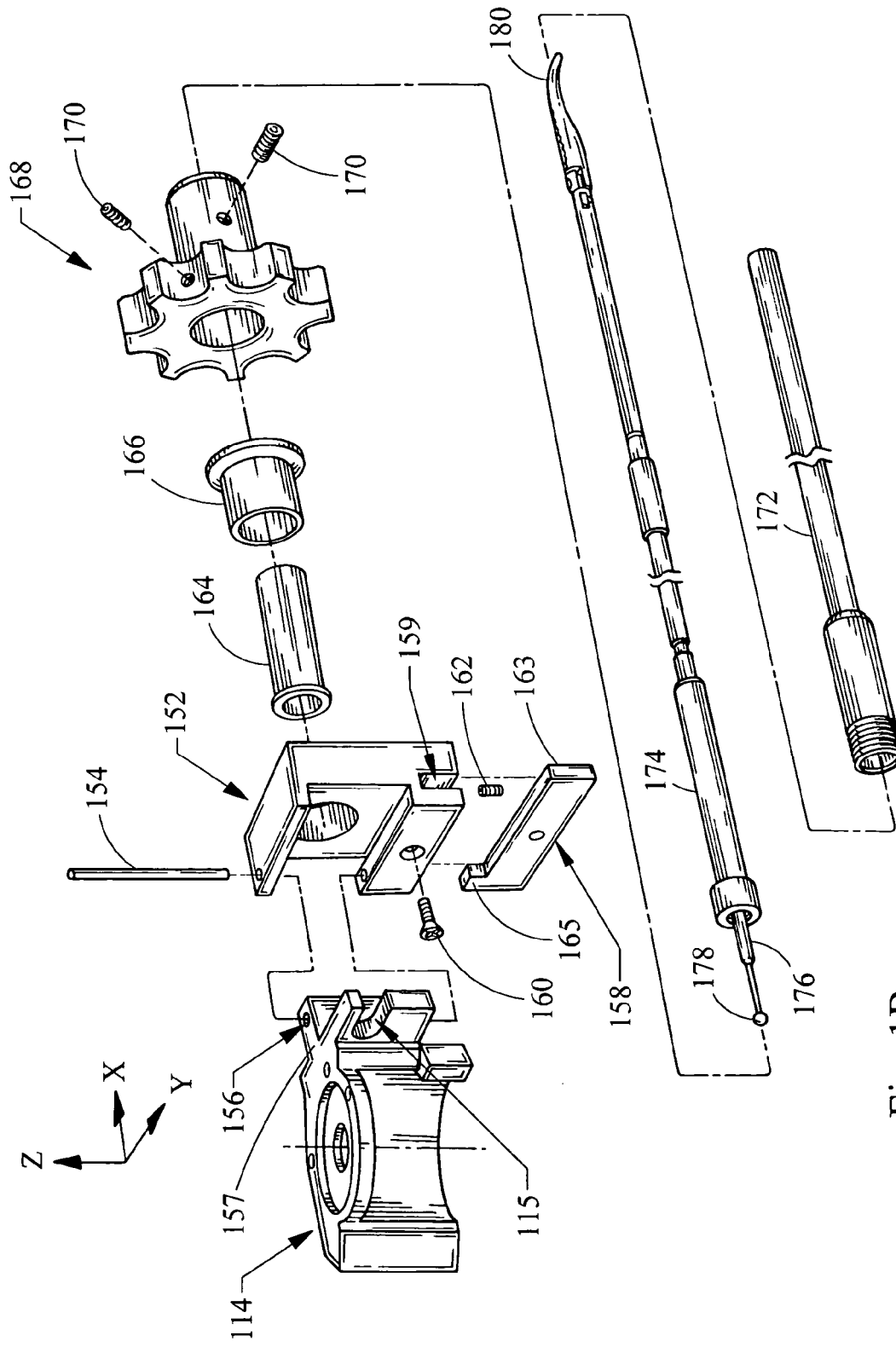
FIG. 1B is an exploded perspective view showing a second portion to the laparoscopic instrument shown in FIG. 1A.
Figure 2:
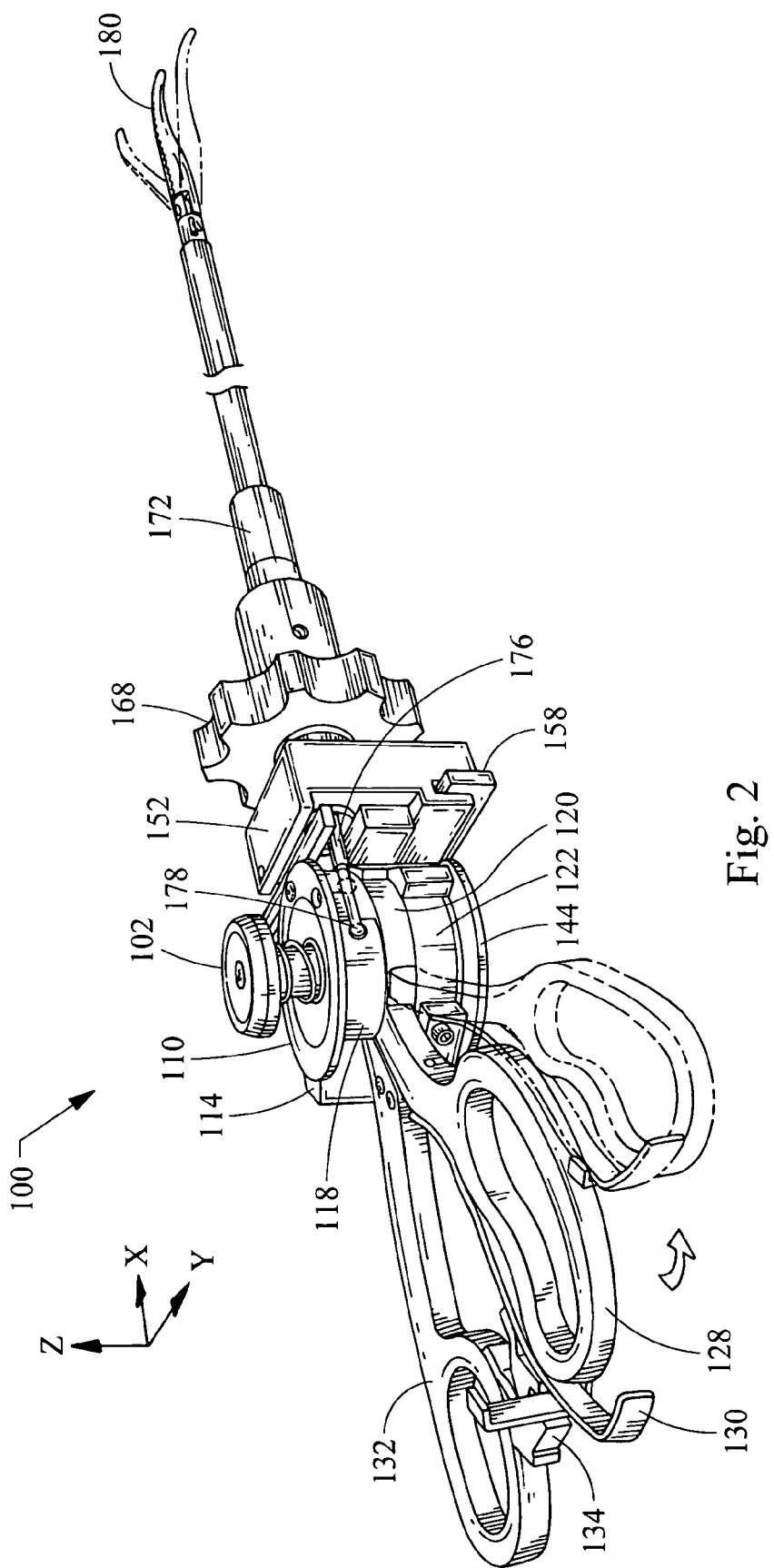
FIG. 2 is an assembly perspective view of the laparoscopic instrument of FIGS. 1A and 1B.

Referring to FIGS. 1A and 1B, a general description of the parts associated with a laparoscopic instrument 100 is provided according to an embodiment of the present invention. A more detailed description of the parts and their associated movements is provided in subsequent drawings. The laparoscopic instrument 100 includes a push button 102 that has a generally cylindrical disk shape. The push button 102 is connected to a winged shaft 104 via a push-button screw 106, which is inserted through a central hole of the push button 102. The push button 102 is adjacent to a spring 108, which includes one end that is in contact with the push button 102 and another end that is in contact with a tool cover 110.

The tool cover 110 is a generally cylindrical plate that includes a central hole and a plurality of tapped periphery holes. The winged shaft 104 protrudes through the central hole of the tool cover 110 toward the push button 102. Two connecting screws 112 connect the tool cover 110 to a housing 114.

The housing 114 includes a drum receiving portion 116 for accommodating at least in part a tool drum 118, a trigger drum 120, and a fixing drum 122, each of which is located adjacent to one another as shown. The housing 114 further includes a ball-receiving slot 115 for allowing pivoting movement of the housing 114, as described in more detail below in reference to FIGS. 17-19.

Referring to FIG. 1AI, the tool drum 118 is illustrated as being generally cylindrical, having a central through-hole, which is cylindrically shaped, and including a plurality of slots through which the winged shaft 104 protrudes. Although the plurality of slots is shown having three slots, alternatively, any number of slots may be used. The slot height extends only through part of the tool drum 118 (i.e., the slots are not through-slots). For example, the slot height is half the height of the tool drum 118. In alternative embodiments, the slot height extends through the entire tool drum 118. In yet other alternative embodiments, the central hole can have any other three-dimensional shape, e.g., a partial toroid, for receiving the winged shaft 104 therethrough. As explained in more detail below, the slots of the tool drum 118 engage the winged shaft 104 for securing the tool drum 118 to the fixing drum 122 in any one of a plurality of positions.

A drum washer 124 and a plug 126 is located between the tool drum 118 and the housing 114. The tool drum 118 includes a ball-receiving hole 127 along its periphery as shown.

The trigger drum 120 is generally cylindrical and is attached to a trigger handle 128 that includes a latching mechanism 130. The trigger drum 120 is attached to the trigger handle 128 directly or through a mechanical linkage. The trigger drum 120 includes a central slotted hole having substantially the same shape and dimensions as the slotted hole of the tool drum 118 through which the winged shaft 104 protrudes. The fixing drum 122 is generally cylindrical and is attached to a fixing handle 132 that includes a locking part 134 for the latching mechanism 130. The fixing drum 122 is attached to the fixing handle 132 directly or through a mechanical linkage. The fixing drum 122 includes a central slotted hole having substantially the same shape and dimensions as the slotted holes of the tool drum 118 and the trigger drum 120 through which the winged shaft 104 protrudes. The fixing drum 122 further includes a plurality of fixing holes 135 for securing the fixing drum 122 as described in more detail below.

The winged shaft 104 includes a generally cylindrical shaft 136 and a plurality of winglets 138, which are arranged in two symmetrical pairs along the shaft 136. The winglet end of the winged shaft 104 is attached to a locking plate 140 via a locking screw 142. In alternate embodiments, the winglets 138 can be splines or parts thereof, keys, or pins.

A fixing cover 144 is located along the winged shaft 104, between the locking plate 140 and the fixing drum 122. The fixing cover 144 includes a central slotted hole having substantially the same shape and dimensions as the slotted holes of the tool drum 118, the trigger drum 120, and the fixing drum 122 through which the winged shaft 104 protrudes. In addition, the fixing cover 144 includes a plurality of push-pin receiving holes through which corresponding push pins 146 are inserted. The push pins 146 protrude through the locking plate 140, the fixing cover 144, and the fixing holes 135 to secure the fixing drum 122 to the locking plate 140.

The locking plate 140 includes a recessed groove 148 for receiving the winged shaft 104 and a plurality of push-pin receiving holes through which corresponding push pins 146 are inserted. A locking washer 150 is inserted between the head of the locking screw 142 and the locking plate 140.

Turning now to FIG. 1B, the housing 114 is pivotably connected to a hinge 152 via a hinge pin 154, which is inserted through a plurality of hinge pivot holes 156. The housing 114 is attached to the hinge 152 at a housing pivoting portion 157, which is inserted in a hinge slotted area of the hinge 152.

The hinge 152 includes a locking lever 158, which is attached to the hinge 152 via a lever screw 160. The locking lever 158 is inserted in a lever slot 159, which is located at a bottom end of the hinge 152. A lever spring 162 is positioned within the lever slot 159 for maintaining the locking lever 158 in a closed position. The locking lever 158 includes an actuating end 163 and a locking end 165. The actuating end 163 is actuated by urging the locking lever 158 toward the lever spring 162 to unlock the hinge 152 from a closed position to an open position, as described in more detail below in reference to FIGS. 17-19. When the locking lever 158 is pressed, it rotates around the axis of the lever screw 160 such that the locking end 165 causes the hinge 152 to pivot about the axis of the hinge pin 154 (the Z-axis).

A long bearing 164 and a short bearing 166 are used to rotatably attach a knob 168 to the hinge 152. A plurality of set-screws 170 are screwed into the knob 168 for retaining the long bearing 165 and the short bearing 166 relative to the knob 168.

A knob extension or sleeve 172 is attached to the knob 168 using a threaded end of the knob extension 172. The knob extension 172 is a hollow shaft (or sleeve) that is used for accommodating a tool holder 174, which is inserted into the hollow of the knob extension 172. The tool holder 174 is a hollow shaft that accommodates a tool 176, which includes a ball 178 at an insertion end and a scissors device 180 at an operating end. The tool 176 is inserted into the tool holder 174, as shown. According to the shown embodiment, the scissors device 180 is a three-member claw device. The outer surface of the sleeve 172 may be composed of or coated with an insulating material, such as Teflon, to electrically insulate the operator of the instrument 100 from the sleeve 172 when using an electric tool such as a cauterizing tool. For example, the sleeve 172 is wrapped with a Teflon shrink tube.

FIGS. 2-8 show various views of the laparoscopic instrument 100 in an assembled form and depict representative movements of the trigger handle 128. The tool drum 118, the trigger drum 120, and the fixing drum 122 are assembled together with the housing 114. The trigger handle 128 and the fixing handle 132 are shown in a locked position, which is described in more detail below. The housing 114 and the hinge 152 are shown in a closed position, and the ball 178 is received by the ball-receiving hole 127 of the tool drum 118.

As represented by the phantom lines, the trigger handle 128 is rotated relative to the fixing handle 132 in a counter clockwise direction (from the locked position) to open the scissors device 180 at the operating end of the tool 176. In general, the rotation of the trigger handle 128 causes the rotation of the tool drum 118, which in turn causes the linear movement of the tool 176. The linear movement of the tool 176 causes an opening/closing movement for the scissors device 180. The relationship between the three drums 118, 120, 122 (also referred to as the drum sandwich assembly) is described in more detail below.

Figure 3:
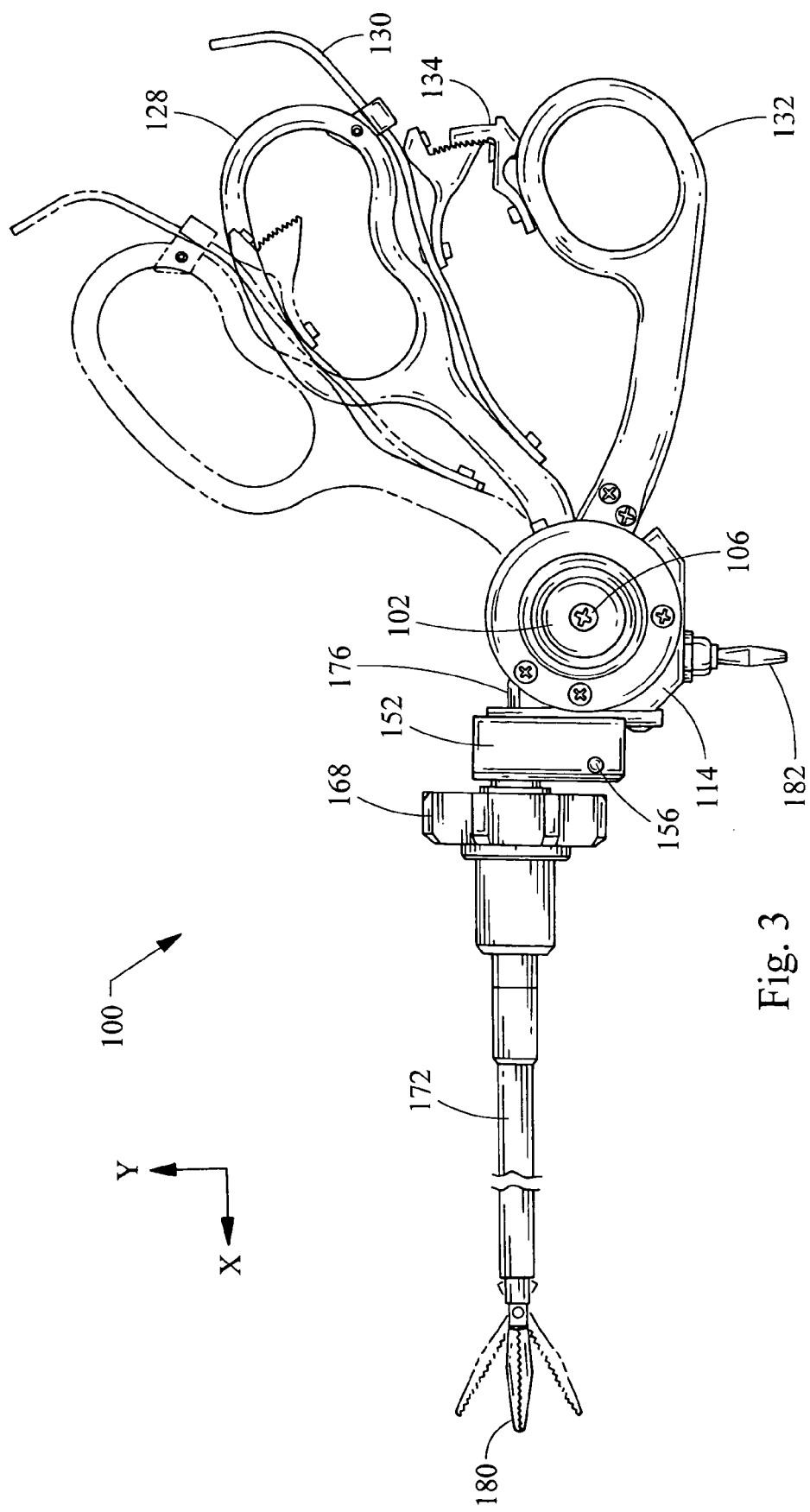
FIG. 3 is a front view of the laparoscopic instrument of FIGS. 1A and 1B.
Figure 4:
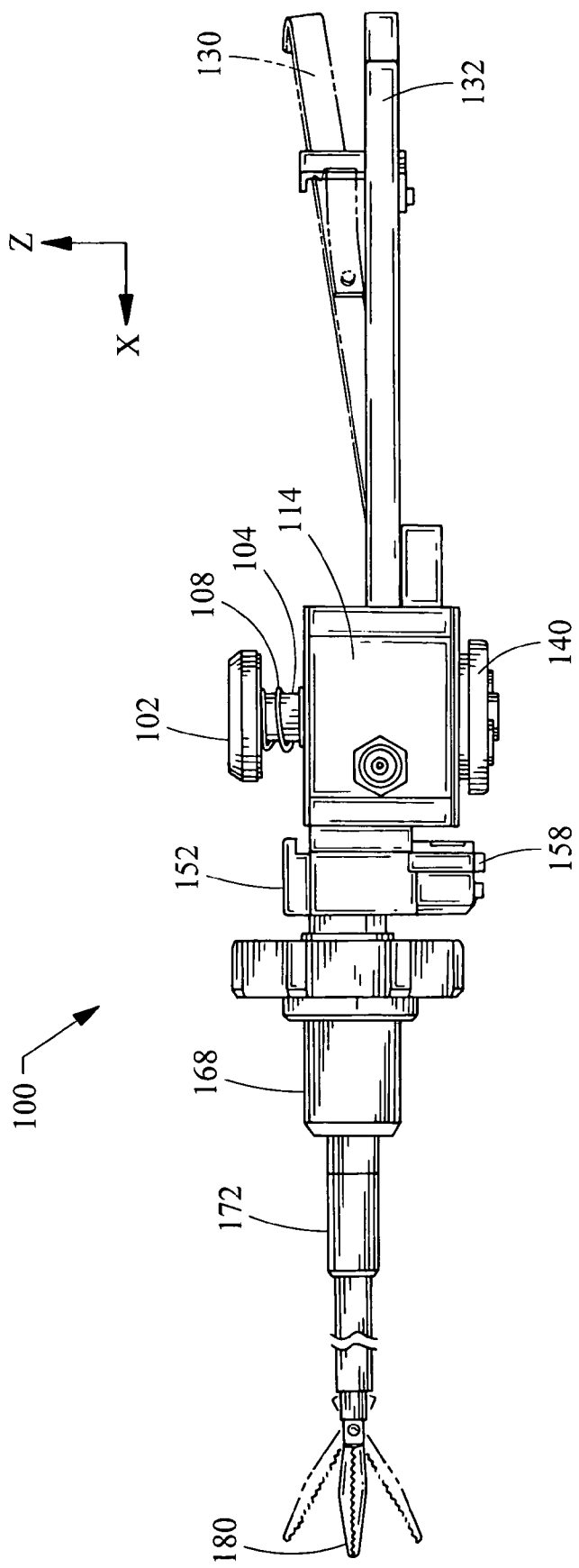
FIG. 4 is a top view of the laparoscopic instrument of FIGS. 1A and 1B.
Figure 5:
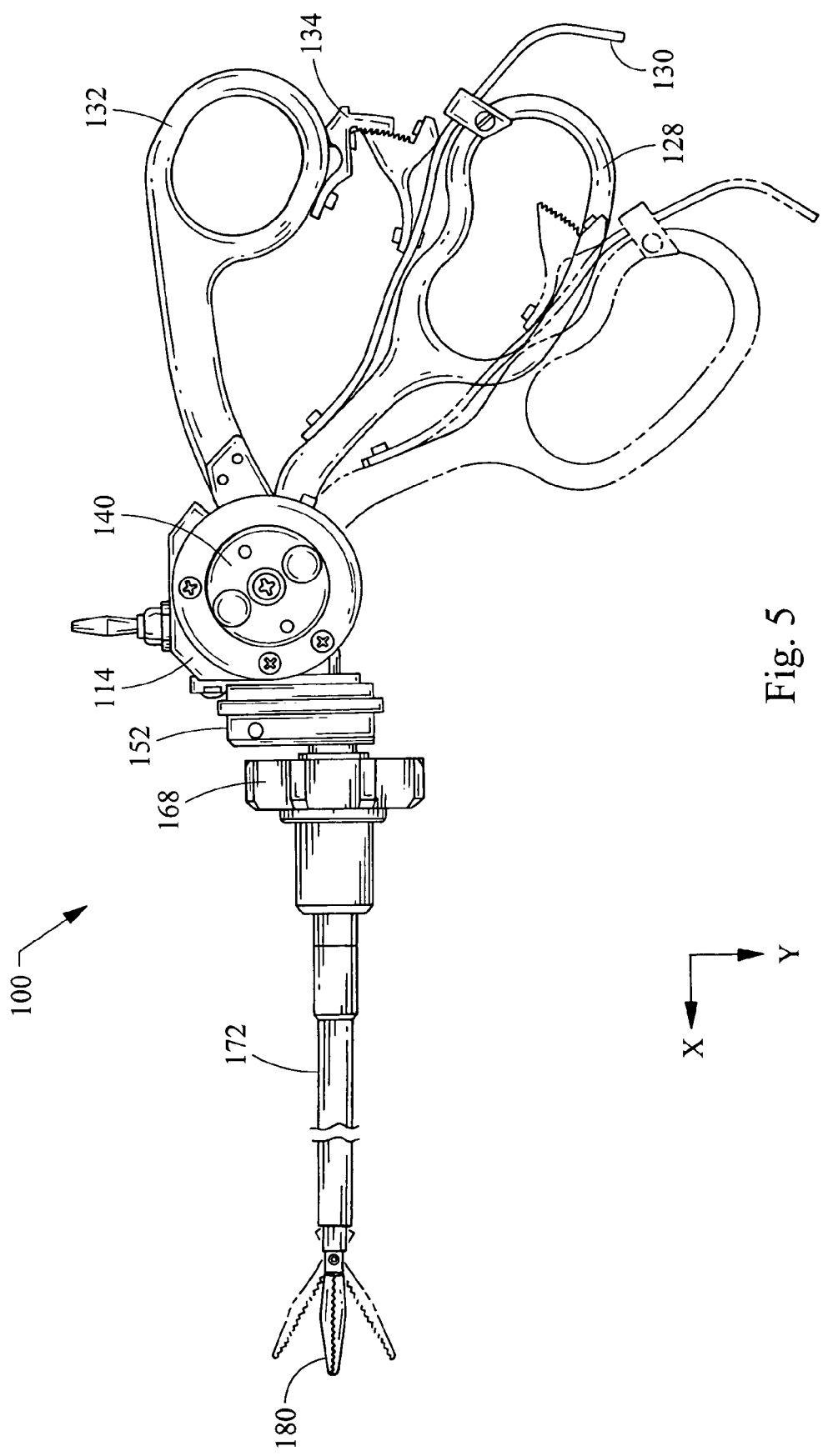
FIG. 5 is a back view of the laparoscopic instrument of FIGS. 1A and 1B.
Figure 6:
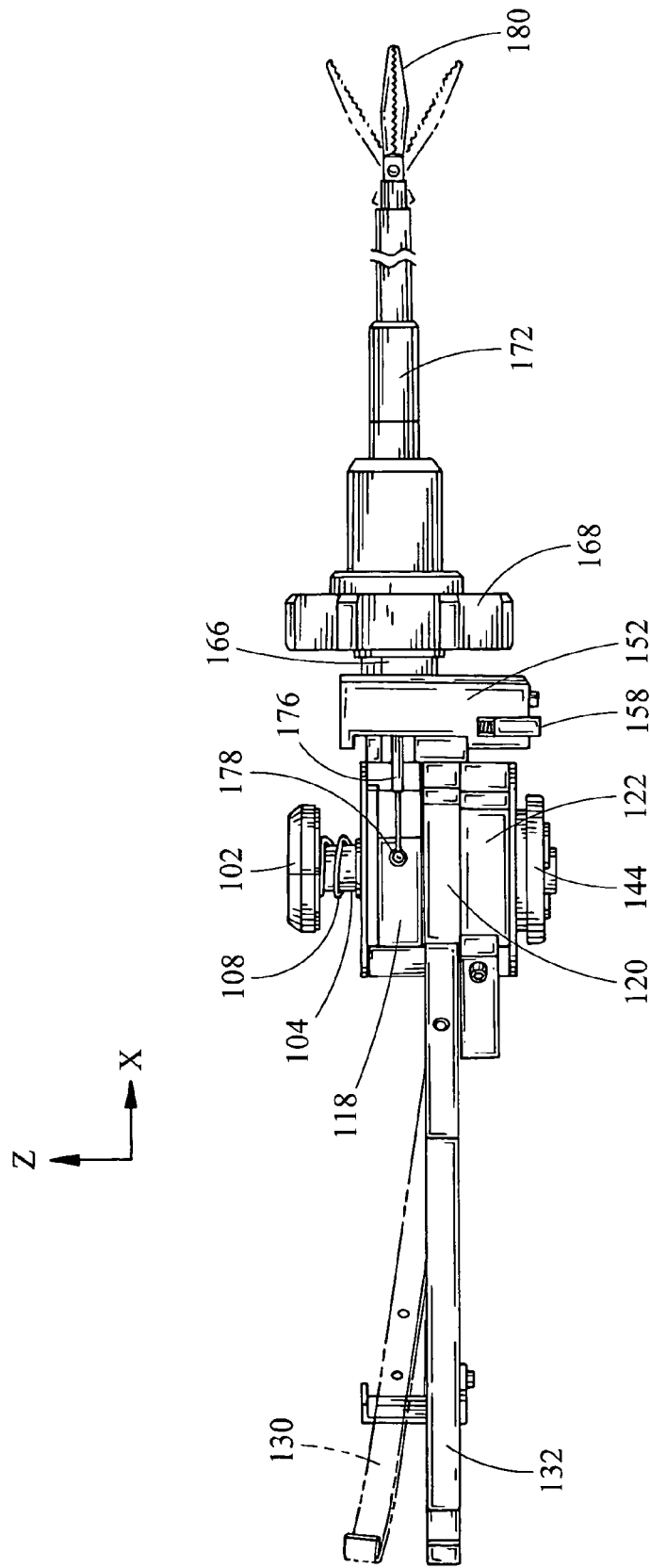
FIG. 6 is a bottom view of the laparoscopic instrument of FIGS. 1A and 1B.
Figure 7:
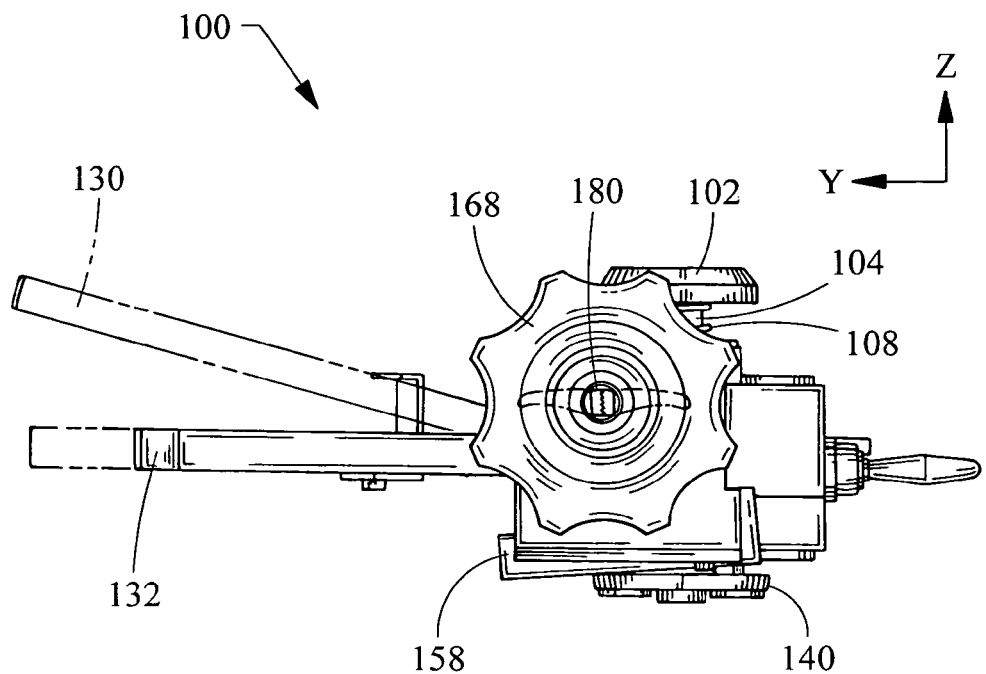
FIG. 7 is a left-side view of the laparoscopic instrument of FIGS. 1A and 1B, showing a tool end of the laparoscopic instrument.
Figure 8:
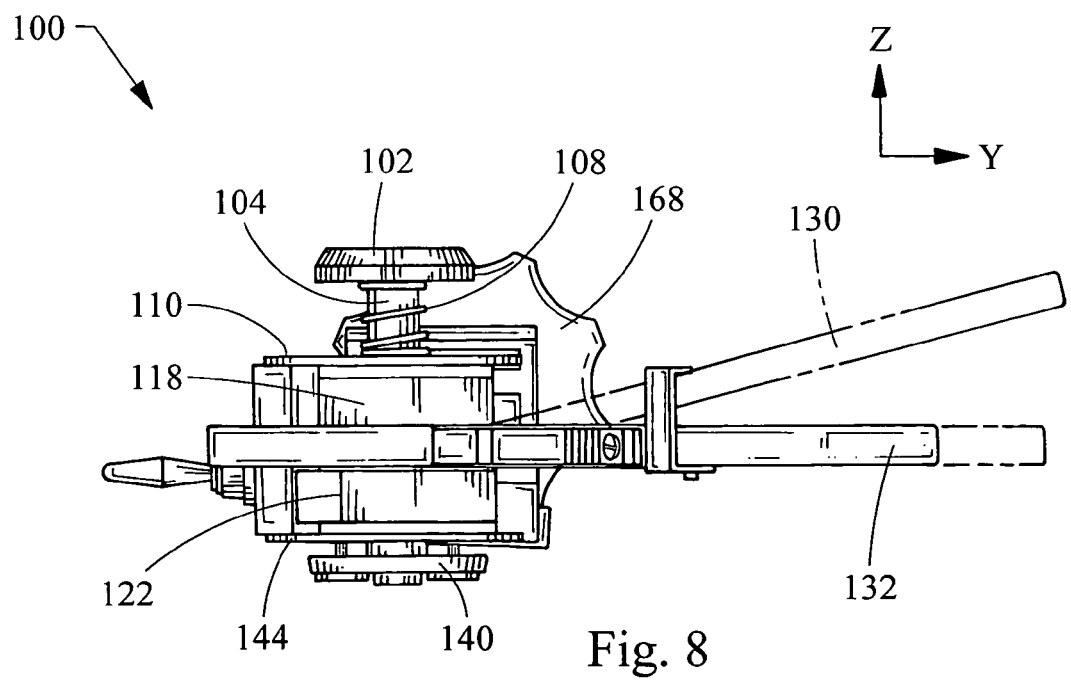
FIG. 8 is a right-side view of the laparoscopic instrument of FIGS. 1A and 1B, showing a handle-end of the laparoscopic instrument.

In addition, as best seen in FIG. 3, the position of the shaft 136 (represented by the push-button screw 106) can be aligned with the hinge pivot hole 156 or can be different than the position of the hinge pivot hole 156. For example, the center of the shaft 136 can be at the same distance in the Y-axis direction from the X-axis of the tool 176 as the hinge pivot hole 156. Alternatively, the distance between the center of the shaft 136 and the X-axis of the tool 176 can be smaller or greater than the distance between the hinge pivot hole 156 and the X-axis of the tool 176.

An electrical probe 182 is protruding from and is attached to the housing 114. The electrical probe 182 is electrically coupled to the tool 176 (such as a cauterizing tool) to supply electrical current from an external power supply. For example, electrical current is supplied via the electrical probe 182 to an electrocautery tool 176 for cauterizing organ tissue during a surgical procedure. Alternatively, a hole or plug is formed in the housing 114 for receiving an electrode therein.

Figure 9:
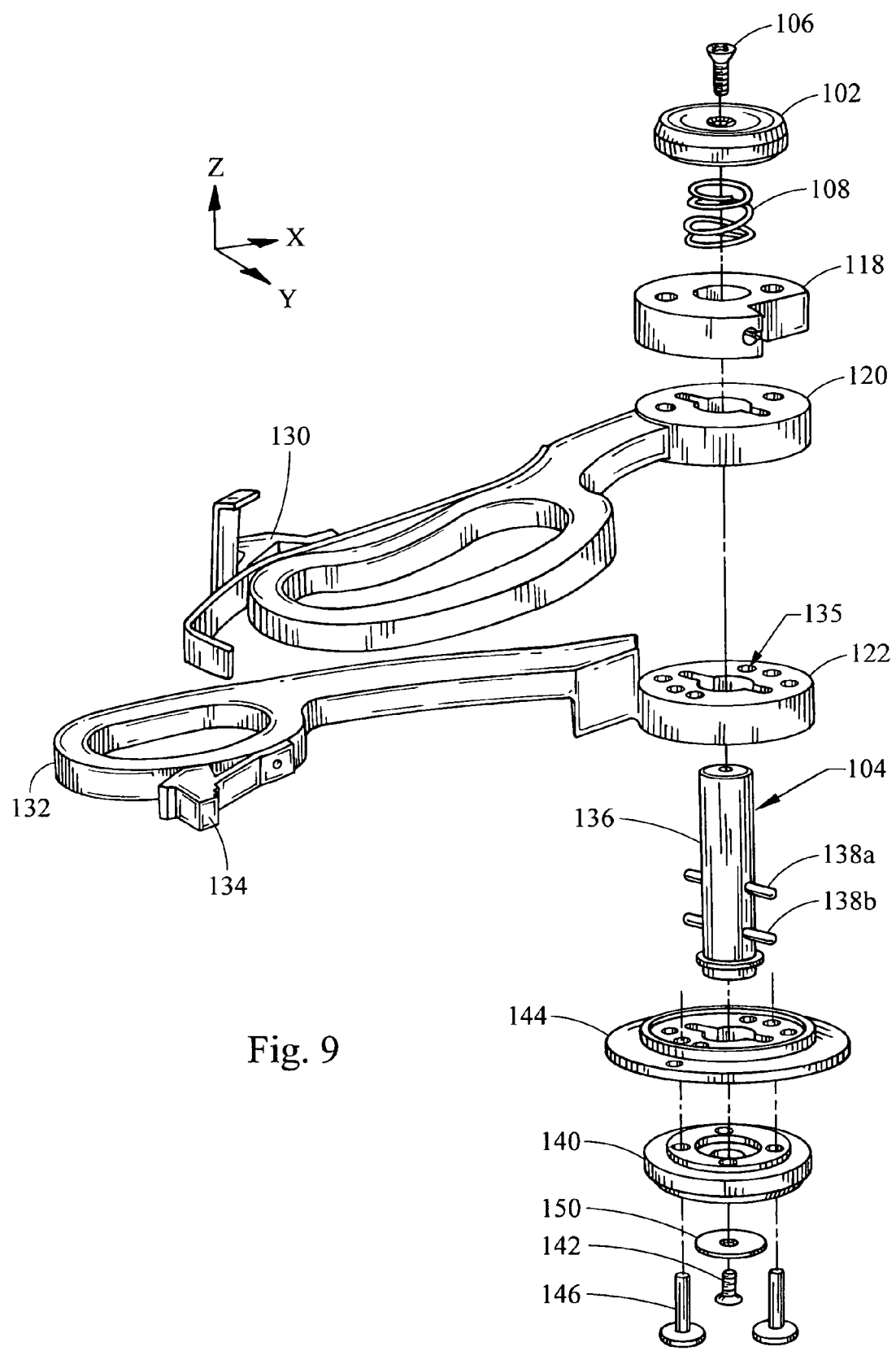
FIG. 9 is an exploded perspective view showing a drum subassembly of the laparoscopic instrument of FIGS. 1A and 1B.
Figure 10:
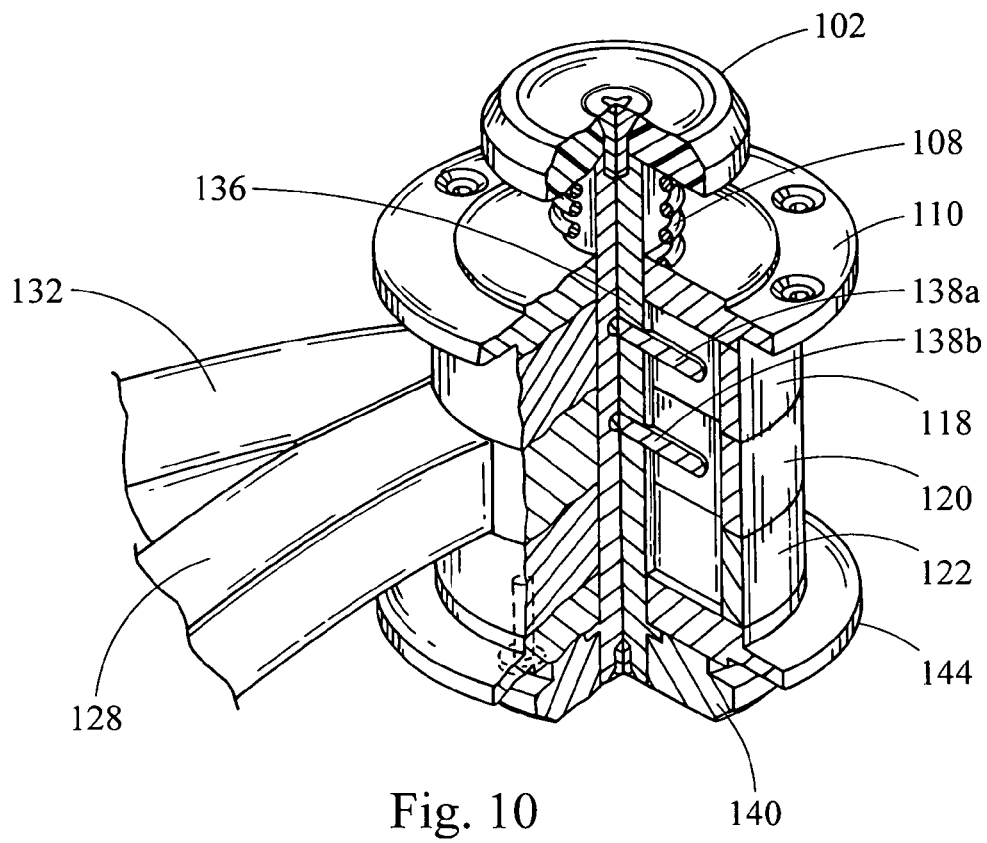
FIG. 10 is an assembly perspective view showing interior details of the drum subassembly of FIG. 9.
Figure 11:
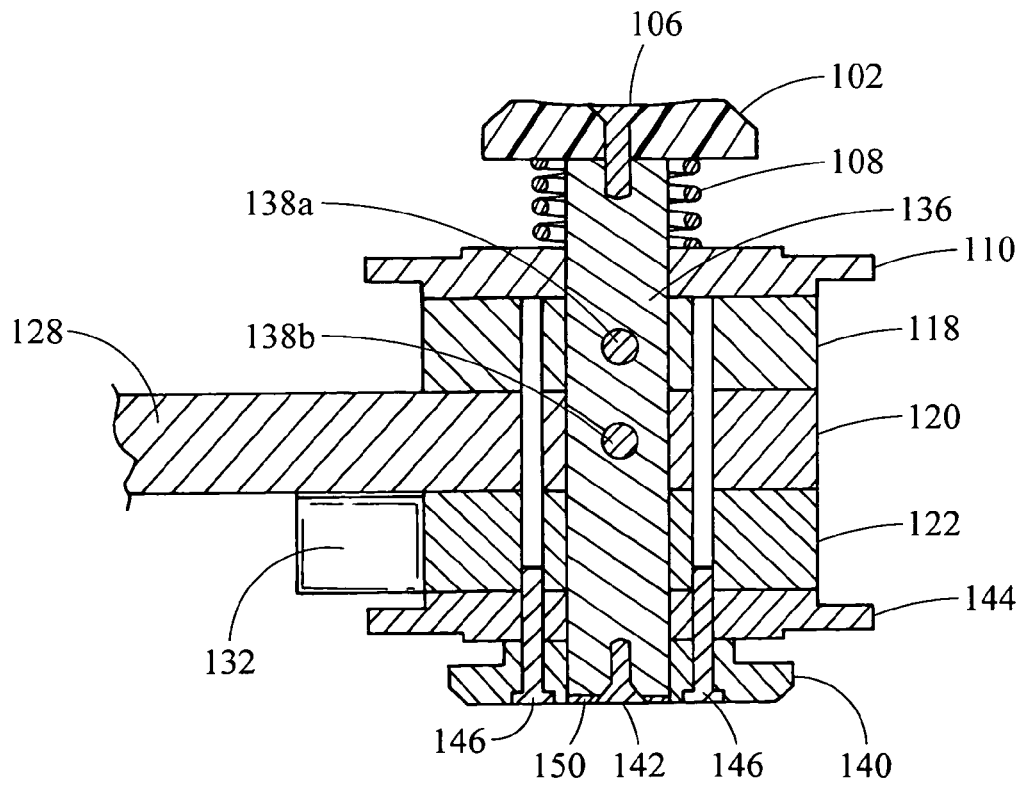
FIG. 11 is a planar cross-sectional view of the drum subassembly of FIG. 9.

Referring to FIGS. 9-11, the tool drum 118, the trigger drum 120, and the fixing drum 122 are sandwiched between the tool cover 110 (located at the top, adjacent to the tool drum 118) and the fixing cover 144 (located at the bottom, adjacent to the fixing drum 122). The push button 102 is located at the top of the drum sandwich assembly—near the tool cover 110—and the locking plate 140 is located at the bottom of the drum sandwich assembly—near the fixing cover 144. The shaft 136 protrudes through each of the fixing cover 144, the fixing drum 122, the trigger drum 120, the tool drum 118, and the tool cover 110. The shaft 136 is attached via the locking screw 142 to the locking plate 140 and via the push-button screw 106 to the push button 102. The shaft 136 also protrudes through the spring 108.

The winglets 138 attached to the shaft 136 are adapted to protrude only through corresponding slots of the tool drum 118, the trigger drum 120, the fixing drum 122, and the fixing cover 144. Depending on whether the push button 102 is in a depressed or un-depressed position, the winglets 138 protrude through only some of the tool drum 118, the trigger drum 120, the fixing drum 122, and the fixing cover 144. Depending on the position of the winglets 138, the rotatable movement of the trigger drum 120 is locked with respect to either the tool drum 118 or the fixing drum 122.

The winglets 138 include a pair of top winglets 138a and a pair of bottom winglets 138b. As shown in FIGS. 10-11, the push button 102 is in an un-depressed position in which the top winglets 138a protrude through the tool drum 118 and the trigger drum 120. In the un-depressed position, the rotatable movement of the trigger drum 120 is fixed with respect to the tool drum 118. If the push button 102 is in a depressed position, the top winglets 138a rotate within the trigger drum 120 (where the bottom winglets 138b are located in the un-depressed position), and the bottom winglets 138b rotate within the fixing drum 122. In the depressed position, the rotatable movement of the trigger drum 120 is fixed with respect to the fixing drum 122. The novel arrangement according to the present invention allows the handles 128, 132 to be rotated regardless of the position of the trigger drum 120 relative to the tool drum 118. This aspect advantageously allows the surgeon to manipulate the handles 128, 132 in any drum position. According to the present invention, instead of having to twist or contort the surgeon's body in order to access a hard-to-reach area of a patient's inner cavity, the surgeon simply rotates the drum to achieve a new position and can continue to manipulate the handles 128, 132, which control the tool 176 inside the patient's body. It is advantageous for the handles 128, 132 to be manipulatable even as they are rotated together around the shaft 136.

Figure 12:
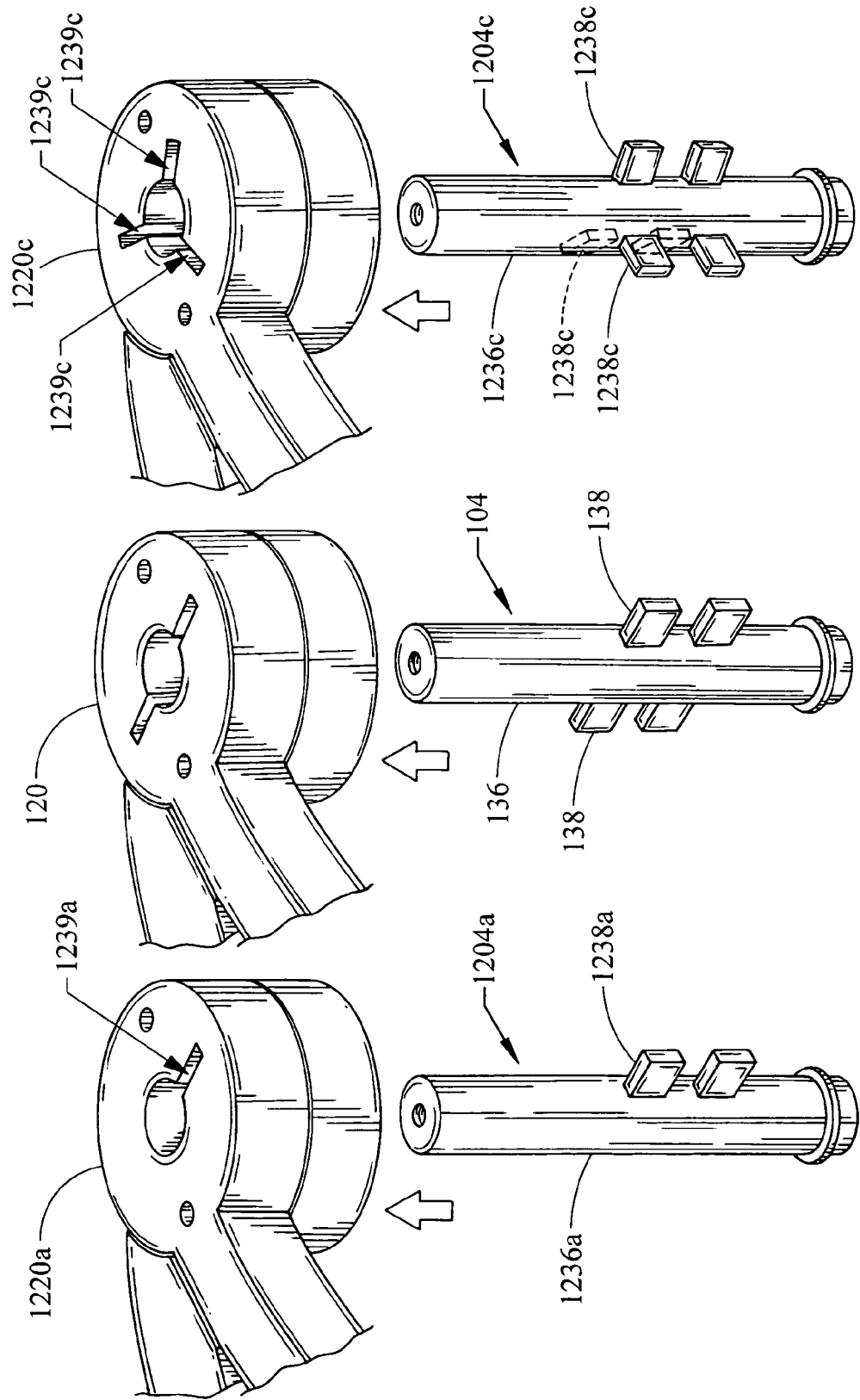
FIGS. 12A-12C are perspective views of an assembly comprising a winged shaft and a handle drum according to three alternative embodiments of the present invention, respectively.

Referring to FIGS. 12A-12C, alternative embodiments of the winged shaft 136 of FIGS. 1-11 are shown depicting three different winglet combinations. For ease of understanding, FIG. 12B shows the winged shaft 104 of FIGS. 1-11, including the shaft 136 and the two sets of winglets 138. In an alternative embodiment, shown in FIG. 12A, a winged shaft 1204a includes a shaft 1236a and a single set of winglets 1238a. To accommodate the single set of winglets 1238a, the holes through which the winged shaft 1204a protrudes (e.g., slotted hole of a trigger drum 1220a) are modified to include a single slot 1239a. Each winglet in the set of winglets 1238a is spaced to lock at most any two drums together when rotated.

In another alternative embodiment, shown in FIG. 12C, a winged shaft 1204c includes a shaft 1236c and three sets of winglets 1238c approximately 120 degrees apart. To accommodate the three sets of winglets 1238c, the holes through which the winged shaft 1204c protrudes (e.g., slotted hole of a trigger drum 1220c) are modified to include three slots 1239c.

Figure 13:
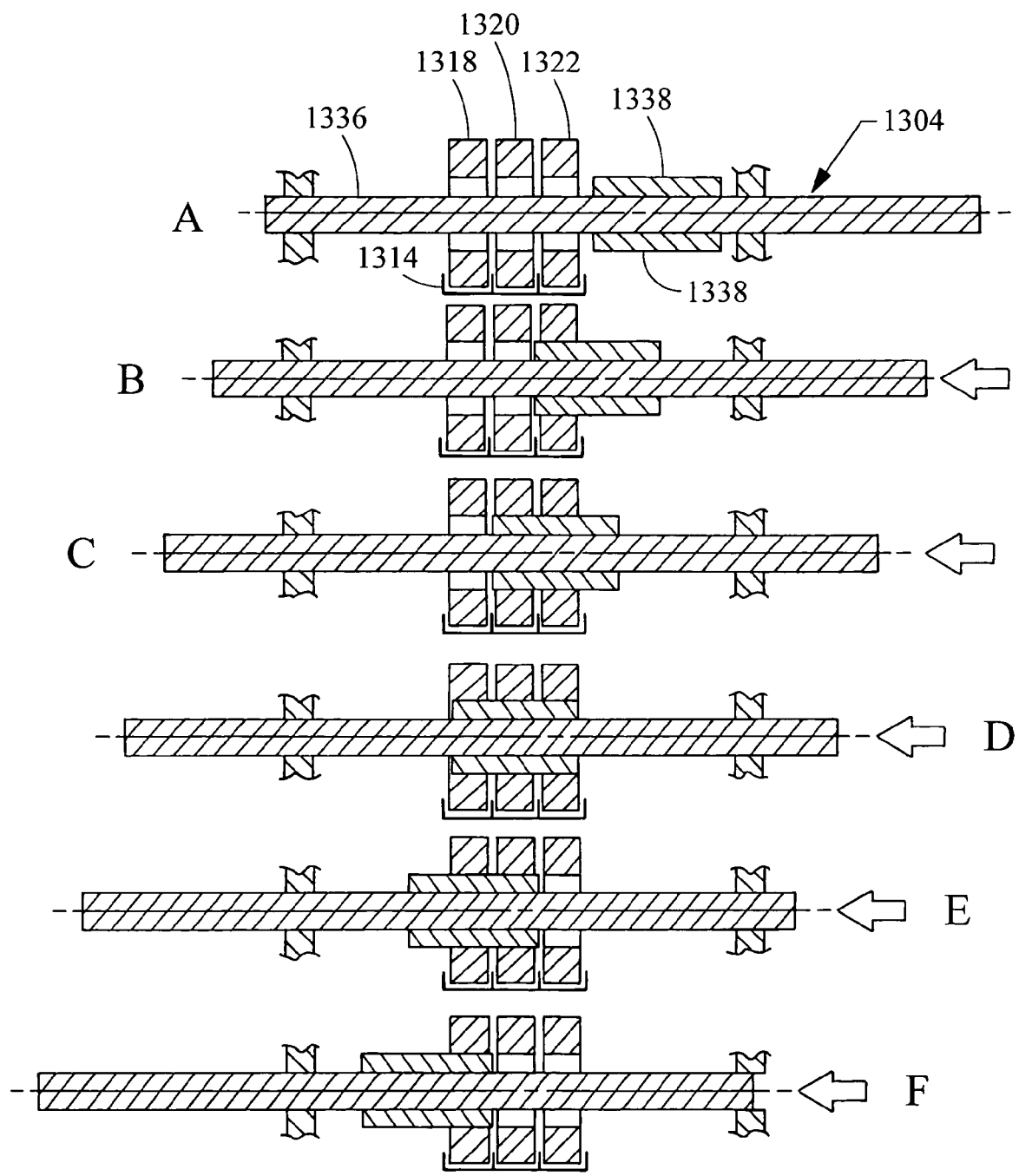
FIG. 13 is a cross-sectional view representing the interaction between a winged shaft and a drum subassembly according to an embodiment of the present invention.

Referring to FIG. 13, a schematic cross-sectional representation illustrates the relationship between a winged shaft 1304 and a plurality of drums, a tool drum 1318, a trigger drum 1320, and a fixing drum 1322, and various positions of the winged shaft 1304 relative to the drums 1318, 1320, 1322. The winged shaft 1304 includes a shaft 1336 and a set of two winglets 1338. From left to right, the drums include the tool drum 1318, the trigger drum 1320, and the fixing drum 1322. The drums 1318, 1320, 1322 are housed within a housing 1314 such that each drum can rotate freely unless fixed in place by the winglets 1338. The drums 1318, 1320, 1322 are fixed from rotational movement when the winglets 1338 protrude through corresponding drum slots. Movement of the winged shaft 1304 interlocks one or more of the drums 1318, 1320, 1322 with respect to each other to achieve a desired rotational combination. For example, as described below, movement of the winged shaft 1304 in any of a plurality of positions A-F achieves any desired rotational combination for the drums 1318, 1320, 1322. As shown in FIG. 13, the winglet and drum combinations can be used to provide a sort of "binary logic" for mechanical devices, such as gears and clutches. The versatility of using the winglets and the drums in accordance with the present invention allows any combination of drum movements to be realized. The concepts of FIG. 13 and related embodiments can be implemented in any mechanical system, including laparoscopic instruments. The present invention expressly contemplates that the lock-and-release embodiments shown and described herein is not limited to laparoscopic instruments.

At position A, the winglets 1338 are positioned to the right of the fixing drum 1322. In this position, each of the drums 1318, 1320, 1322 is free to rotate with respect to each other.

At position B, the winged shaft 1304 is moved toward the drums 1318, 1320, 1322 such that the winglets 1338 are positioned within the fixing drum 1322 only. Accordingly, in this position the fixing drum 1322 is fixed from rotational movement, while the tool drum 1318 and the trigger drum 1320 are free to rotate.

At position C, the winged shaft 1304 is moved further toward the drums 1318, 1320, 1322 such that the winglets 1338 are positioned within both the trigger drum 1320 and the fixing drum 1322. Accordingly, in this position the trigger drum 1320 and the fixing drum 1322 are fixed from rotational movement, while the tool drum 1318 is free to rotate.

At position D, the winged shaft 1304 is moved further toward the drums 1318, 1320, 1322 such that the winglets 1338 are positioned within all three drums. Accordingly, in this position each of the drums 1318, 1320, 1322 is fixed from rotational movement.

At position E, the winged shaft 1304 is moved further toward the drums 1318, 1320, 1322 such that the winglets 1338 are positioned within the tool drum 1318 and the trigger drum 1320. Accordingly, in this position the tool drum 1318 and the trigger drum 1320 are fixed from rotational movement, while the fixing drum 1322 is free to rotate.

At position F, the winged shaft 1304 is moved further toward the drums 1318, 1320, 1322 such that the winglets 1338 are positioned within the tool drum 1318 only. Accordingly, in this position the tool drum 1318 is fixed from rotational movement, while the trigger drum 1320 and the fixing drum 1322 are free to rotate.

Figure 14:
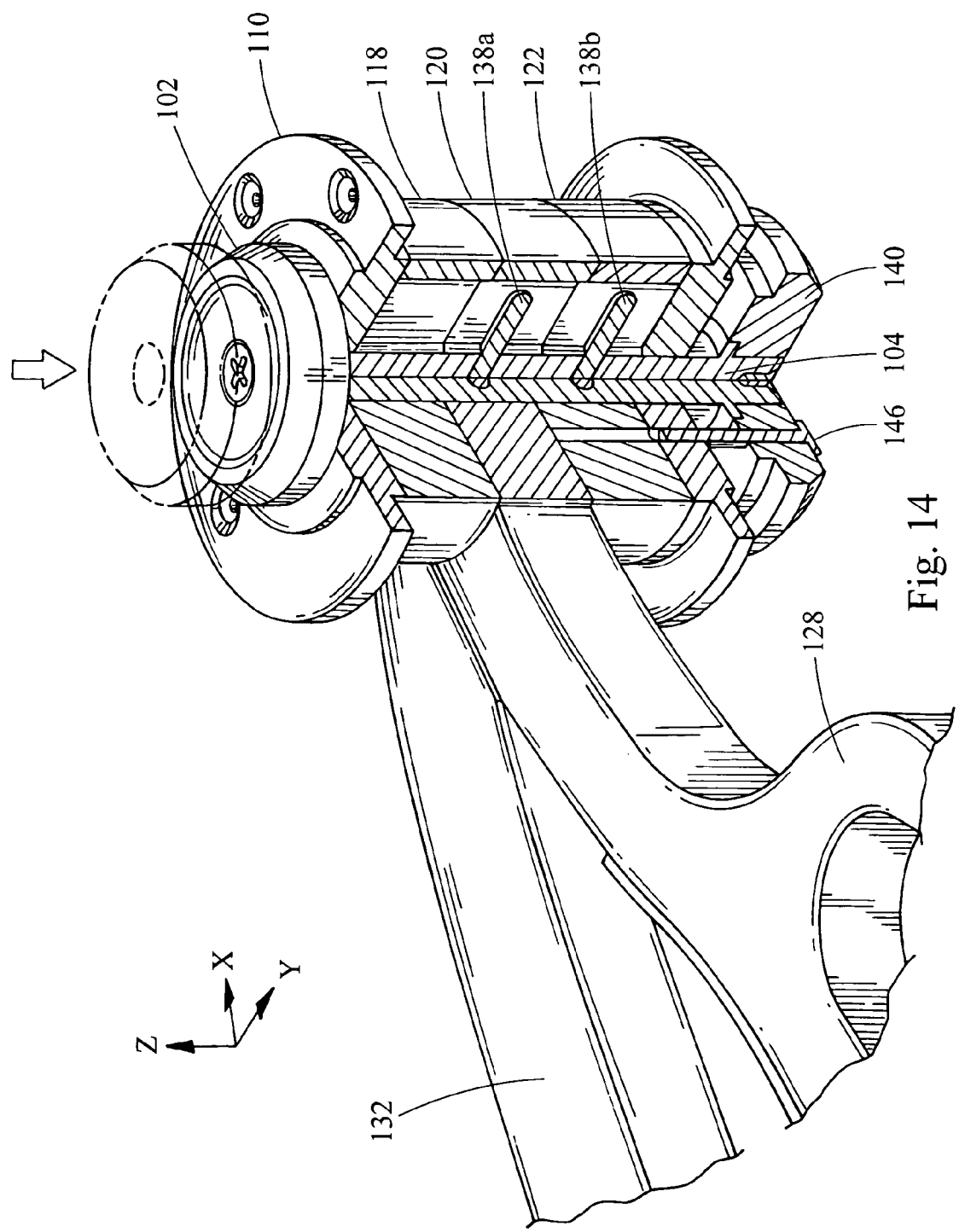
FIG. 14 is a perspective cross-sectional view of the drum subassembly of FIG. 9 showing a push-button in a fully depressed position and a pair of handles in a first position.
Figure 15:
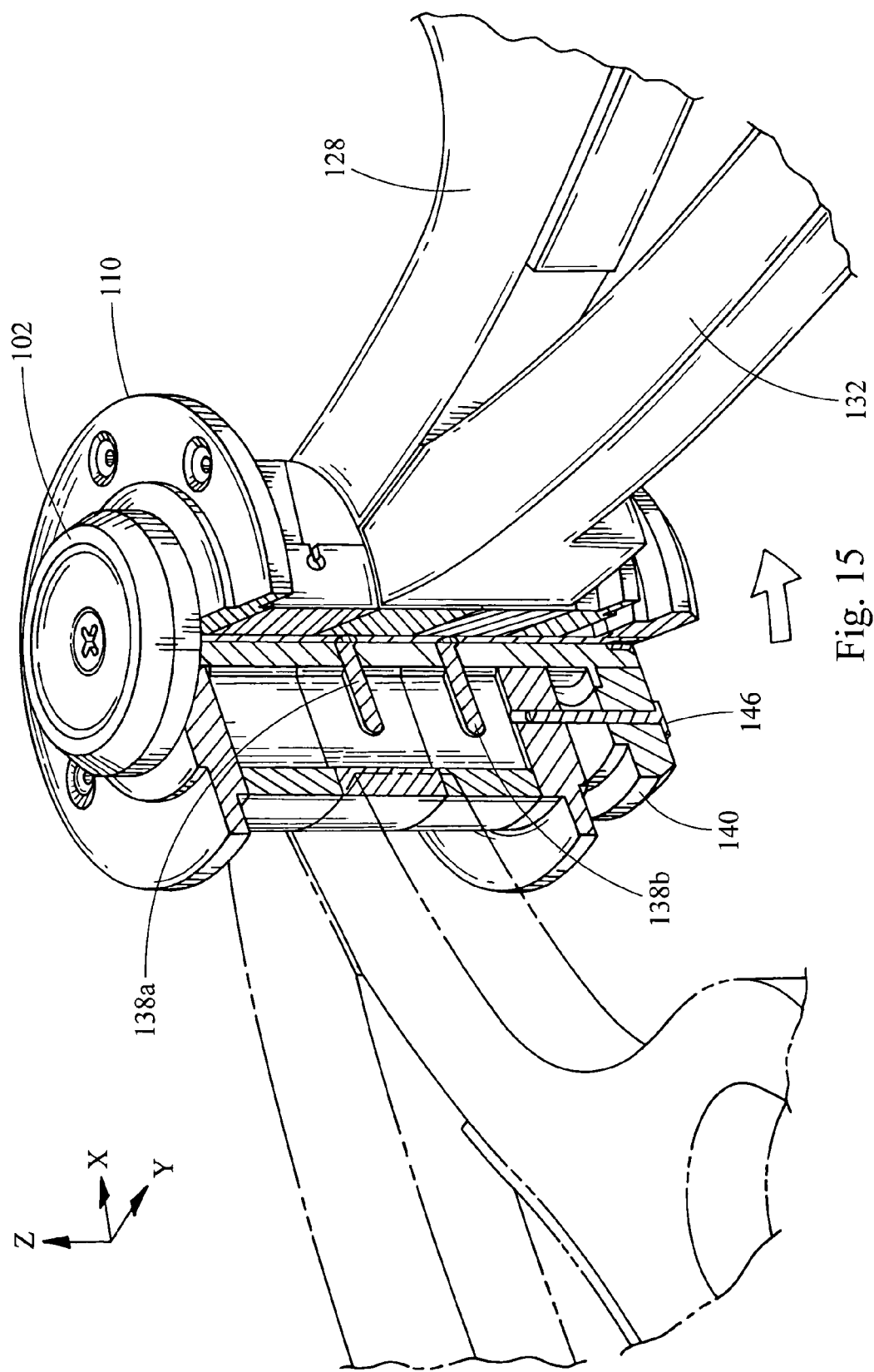
FIG. 15 is a perspective cross-sectional view showing the push-button of FIG. 14 in the fully depressed position and the pair of handles in a second position.
Figure 16:
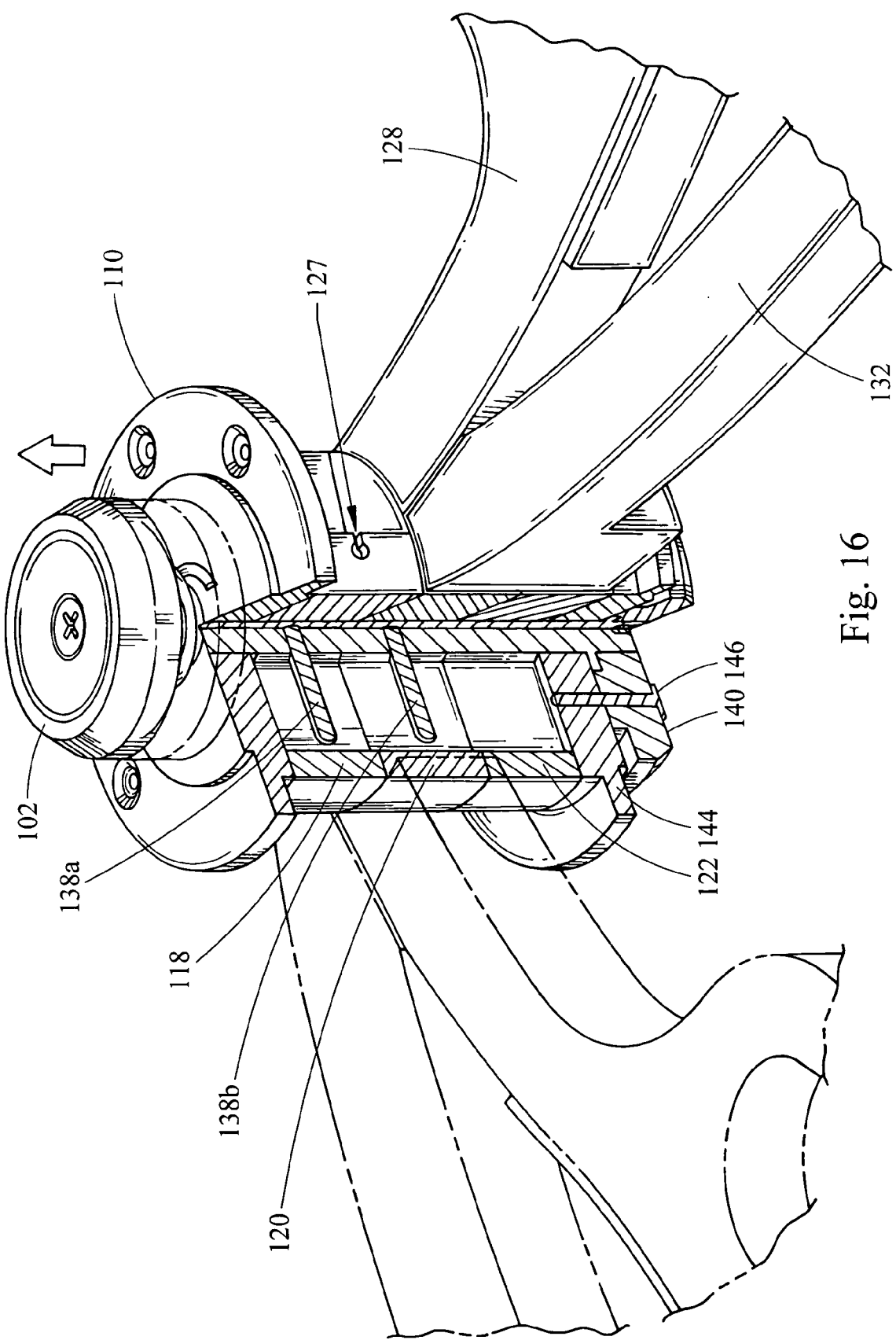
FIG. 16 is a perspective cross-sectional view showing the push-button of FIG. 14 in an un-depressed position and the pair of handles in the second position.

Referring to FIGS. 14-16, a cut-away perspective view of the drums 118, 120, 122 is shown revealing the winged shaft 104 in various positions together with the winglets 138. With reference to these figures, the movement of the winged shaft 104 and of the handles 128, 132 will now be described in more detail. In FIG. 14, the push button 102 is shown in a depressed position, and the handles 128, 132 are shown in a first position. Depressing the push button 102 causes the winged shaft 104 to slide in a direction away from the movement of the push button 102 until the top winglets 138a are located within the trigger drum 120 and the bottom winglets 138b are located within the fixing drum 122. In this configuration, the trigger drum 120 and the fixing drum 122 are fixed or locked together, which in turn locks the handles 128, 132 together. In addition, the locking plate 140 and the push pins 146 are correspondingly urged away from the fixing drum 122, which is now disengaged from the locking plate 140 and the push pins 146.

Accordingly, in the depressed position the trigger drum 120 and the fixing drum 122 are locked with respect to each other. Further, because the fixing drum 122 is now disengaged from the locking plate 140 and the push pins 146, the combination of the trigger drum 120 and the fixing drum 122 is free to rotate around the Z-axis (the axis of the winged shaft 104).

In FIG. 15, the push button 102 remains in the depressed position. However, the handles 128, 132 have been rotated counter clock-wise from the first position to a second position. Thus, the only two components that change their position from the first position to the second position are the trigger handle 128 and the fixing handle 132. For example, the position of the tool drum 118 remains unchanged. By rotating the handles 128, 132 to a new position, while maintaining the position of the tool drum 118, a surgeon using the laparoscopic instrument 100 may be able to achieve a better grasping position for the handles 128, 132 without changing the position of the tool 176 inside a patient and without contorting or twisting the surgeon's body to maintain a comfortable and firm grasp.

As can be seen in FIGS. 1A and 9, the fixing handle 132 is secured to the locking plate 140 by inserting the push pins 146 through the fixing holes 135. Three pairs of fixing holes 135 are shown, and each fixing hole pair represents a different handle position (up to three different positions in the embodiment shown in FIG. 1A). When the push button 102 is depressed, the push pins 146 disengage the fixing holes 135, allowing the fixing drum 122 to freely rotate. The force exerted by the spring 108 allows the surgeon to rotate the fixing drum 122 (and thereby the fixing handle 132) until the push pins 146 "click" into alignment with a different set of fixing holes 135. Although three pairs of fixing holes 135 are shown allowing the fixing handle 132 to be rotated among one of three different positions, fewer or additional fixing holes are contemplated in other embodiments to allow the fixing handle 132 to be rotated among a corresponding number of positions. For example, if four positions are desired, four pairs of fixing holes 135 are formed in the fixing drum 122 and spaced according to each desired position. Although two push pins 146 are shown in FIG. 1A, in other embodiments, a different number of push pins is used instead.

In FIG. 16, the push button 102 is shown in the un-depressed position to engage the fixing drum 122 to the locking plate 140 and the trigger drum 120 to the tool drum 118. The winglets 138 are now located within the tool drum 118 and the trigger drum 120 to secure the tool drum 118 and the trigger drum 120 to each other. The push pins 146 engage the fixing drum 122, fixing the handles 128, 132 in a second position. When the tool drum 118 and the trigger drum 120 are fixed relative to each other, i.e., in the un-depressed position, the trigger handle 128 may be partially rotated. The rotation of the trigger handle 128 causes the rotation of the tool drum 118, which in turn causes the linear movement of the tool 176. The linear movement of the tool 176 allows the surgeon to use the operating end of the tool 176. For example, a counter clock-wise movement of the trigger handle 128 causes the opening of the scissors device 180, while a clock-wise movement of the trigger handle 128 causes the closing of the scissors device 180.

Figure 17:
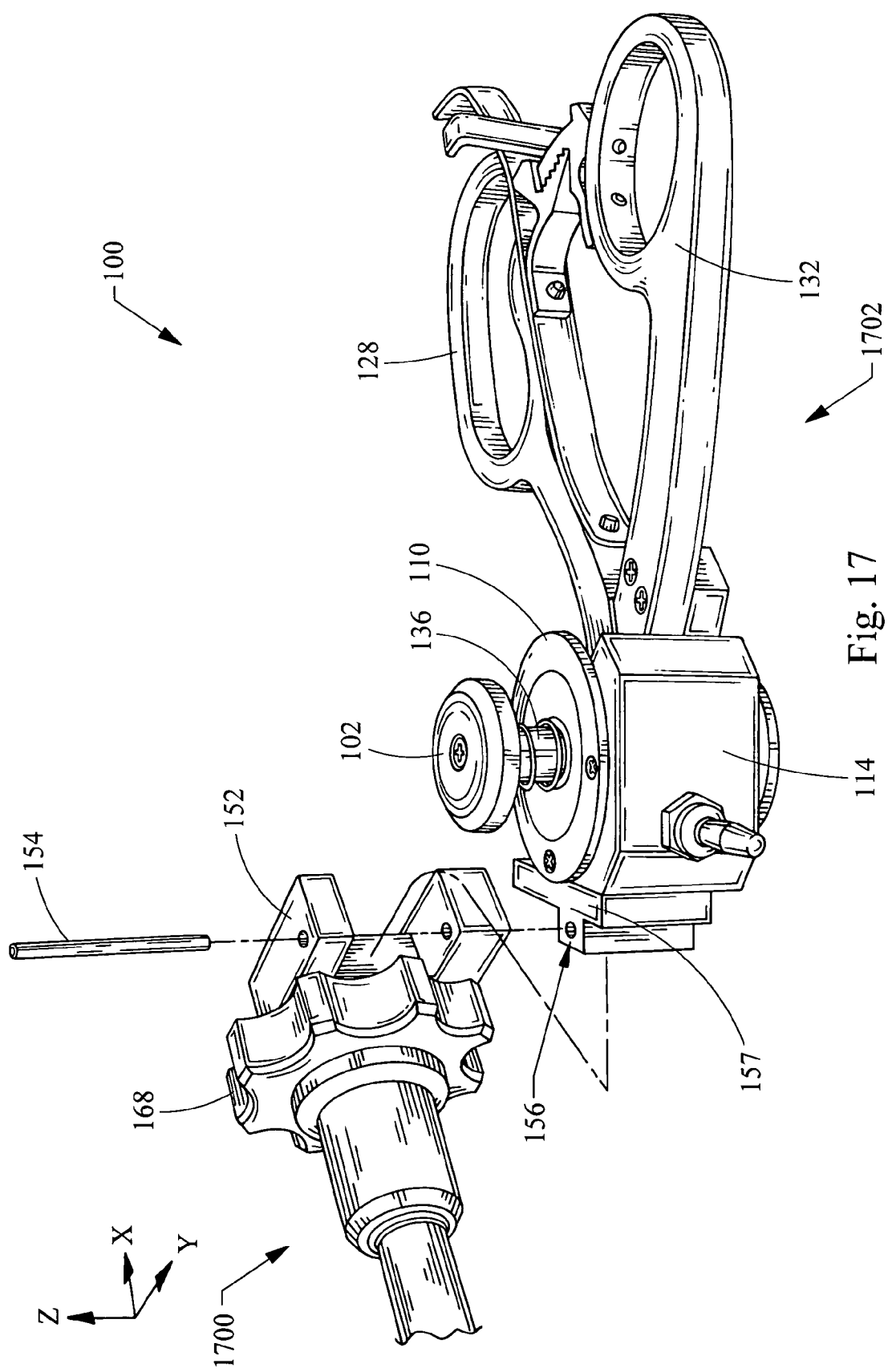
FIG. 17 is a partial exploded perspective view showing a shotgun subassembly of the laparoscopic instrument of FIGS. 1A and 1B in an open breech position.
Figure 18:
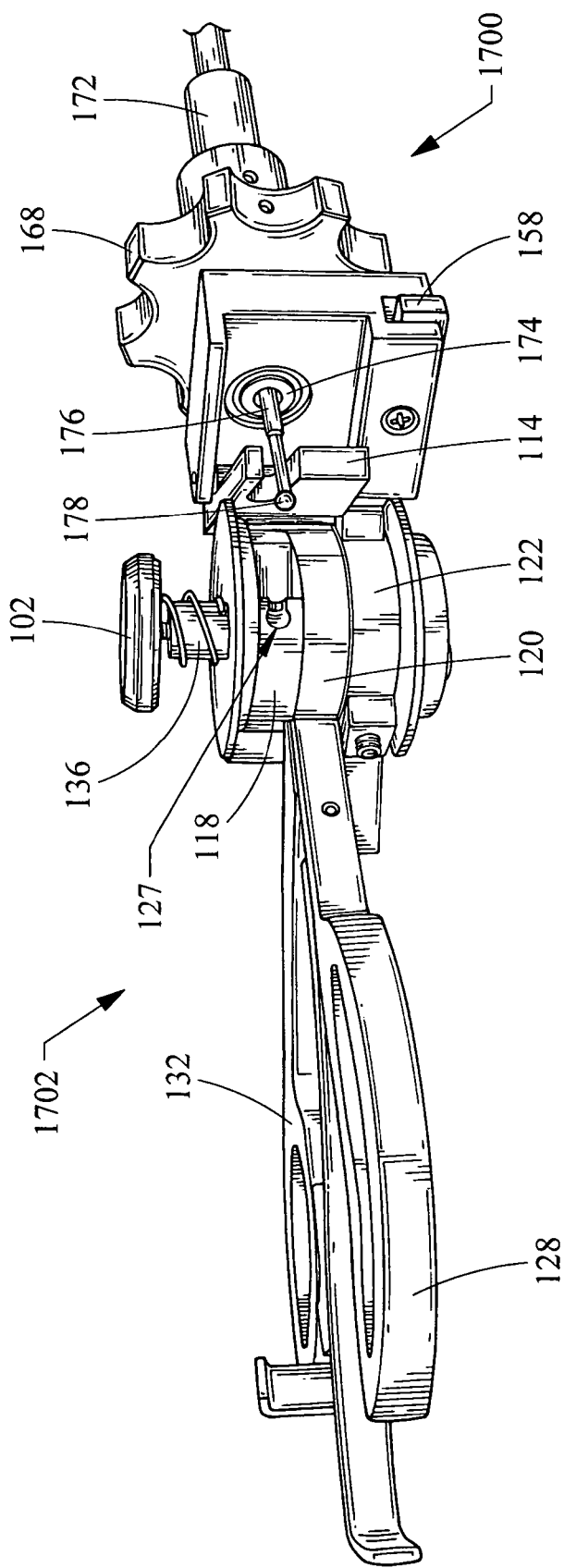
FIG. 18 is a perspective view of the shotgun subassembly of FIG. 17 in an open breech position exposing an insertion end of a laparoscopic tool.

Referring to FIGS. 17-19, there is shown a shotgun subassembly of the laparoscopic instrument 100 in an open "breech" position. The term "shotgun" subassembly refers to the resemblance of the laparoscopic instrument 100 to the breech of a shotgun, which allows the surgeon to replace the laparoscopic tool without removing the instrument 100 from the patient's body. While the instrument 100 is inserted into the patient's body, the shotgun subassembly can be opened and closed like a shotgun to expose one end of the tool for removal and reinsertion. The laparoscopic instrument 100 includes a hinge portion 1700 and a housing portion 1702, which together form the shotgun subassembly having a "breech" that is pivotable about a hinge 152. The hinge portion 1700 generally includes the hinge 152, the tool 176, and the scissors device 180. The housing portion 1702 generally includes the housing 114, the handles 128, 132, and the drums 118, 120, 122. The pivoting of the hinge 152 with respect to the housing 114 of the laparoscopic instrument 100 is described in more detail in connection with FIGS. 18 and 19. In FIG. 17, the hinge 152 is assembled to the housing pivoting portion 157 using the hinge pin 154. The housing 114 pivots about the hinge pin 154 in the Z-axis to provide the opening and/or closing movement of the housing portion 1702 with respect to the hinge portion 1700.

In FIGS. 18 and 19, the hinge portion 1700 is shown in an open position, having been pivoted in a counter clock-wise direction about the Z-axis from the closed position. As the hinge portion 1700 is urged toward the open position, the ball 178—along with the tool 176—is retracted from the ball-receiving hole 127 of the tool drum 118. To open the hinge portion 1700, the locking lever 158 is pressed in a direction toward the tool 176 (as described earlier in reference to FIG. 1B) such that the locking end 165 (shown in FIG. 1B) releases the housing pivoting portion 157. As the hinge portion 1700 is urged toward the open position, the ball 178 passes through the ball-receiving slot 115 formed in the housing 114 until the ball 178 exits the ball-receiving slot 115. After moving the hinge portion 1700 into the open position, the surgeon can remove the tool 176 from within the hinge portion 1700 and replace it with another laparoscopic tool without removing any other part of the instrument 100 from the patient's body. Thus, during the tool replacement, the knob extension or sleeve 172 remains inside the patient in a fixed position. In other words, in contrast to prior art laparoscopic instruments, the surgeon is not required to remove the instrument 100 from within the patient in order to replace the tool 176 with another tool. Maintaining the instrument 100 inside the patient while exchanging tools advantageously eliminates the need for the surgeon to search for and find a previously located body part or position.

The location of the ball-receiving hole 127 is found by drawing a circle about the hinge pin 154, whose radius extends to the end of the ball 178 (when the tool 176 is fully inserted into the knob extension 172). Where the circle intersects the tool drum 118 is where the manufacturer should form the ball-receiving hole 127.

In an alternate embodiment, instead of adapting the hinge portion 1700 to swing open, the hinge portion 1700 is adapted to slide open. For example, instead of having the housing 114 rotatable with respect to the hinge 152, the housing 114 slides open with respect to the hinge 152 in, for example, a direction of the Z-axis, to allow the removal and/or insertion of the tool 176.

Figure 20B:
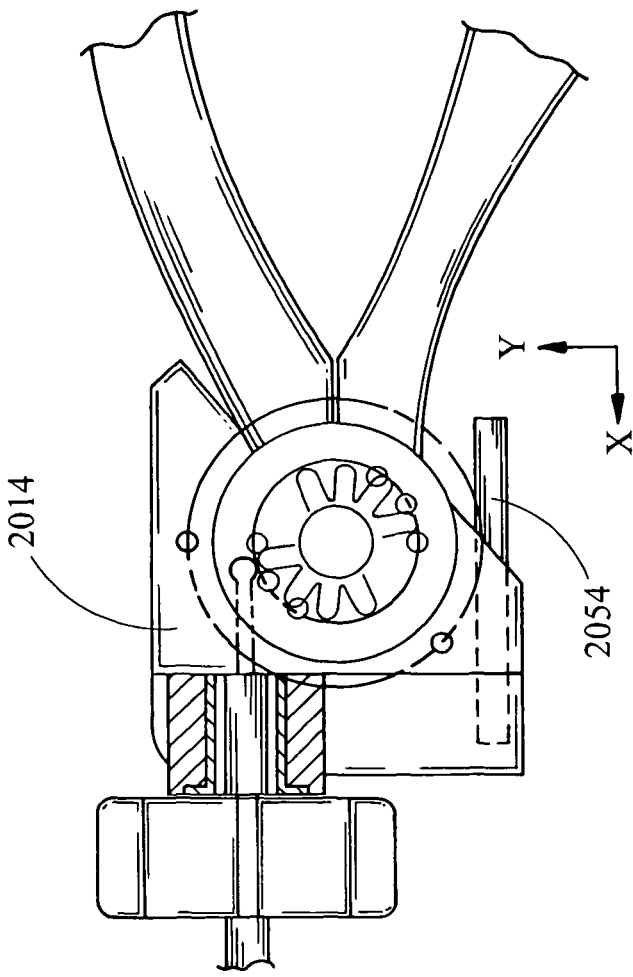
FIG. 20B is a representative side view of FIG. 20A.
Figure 20A:
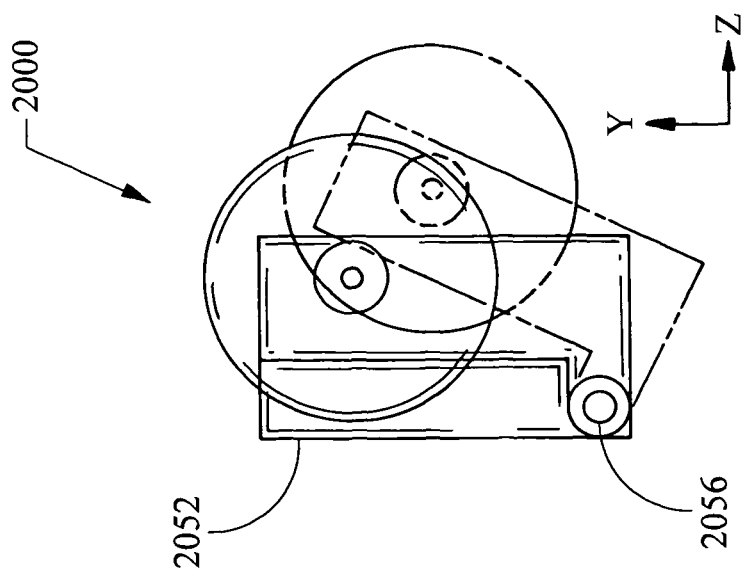
FIG. 20A is a representative diagrammatic front view showing an alternative embodiment of a shotgun subassembly rotating about an X-axis of a laparoscopic instrument.

Referring to FIGS. 20A and 20B, an alternative embodiment of the present invention shows a laparoscopic instrument 2000 that includes a housing 2014 and a hinge 2052. The hinge 2052 pivots around an X-axis of the laparoscopic instrument 2000. Specifically, the hinge 2052 pivots around a hinge pin 2052, which is inserted through a hinge pivot hole 2056, with respect to the housing 2014.

Figure 21A:
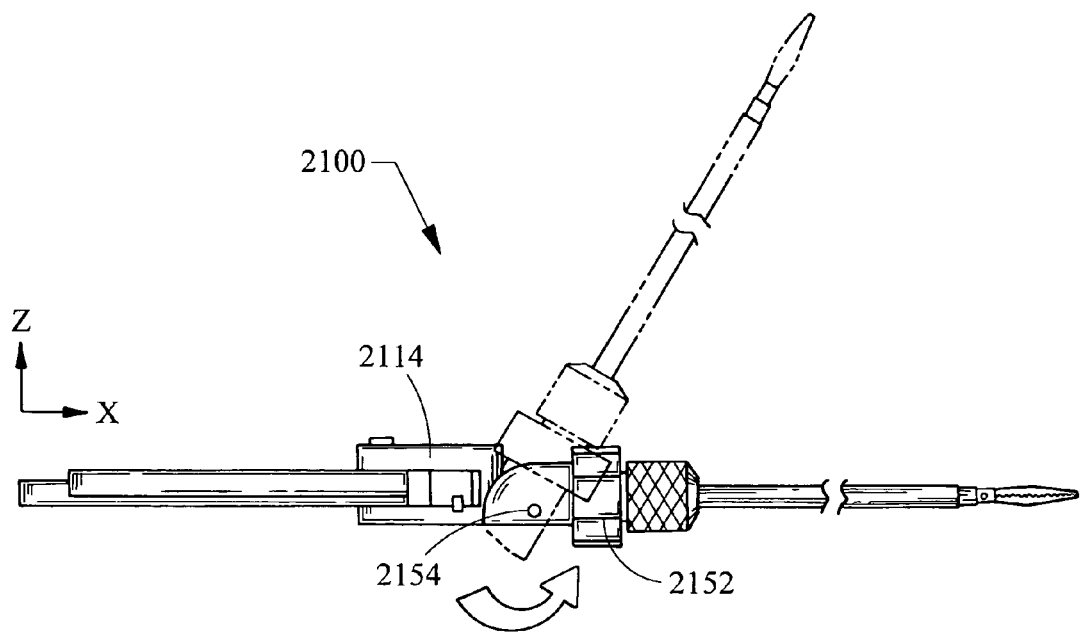
FIG. 21A is a representative top view showing another alternative embodiment of a shotgun subassembly rotating about a Y-axis of a laparoscopic instrument.
Figure 21B:
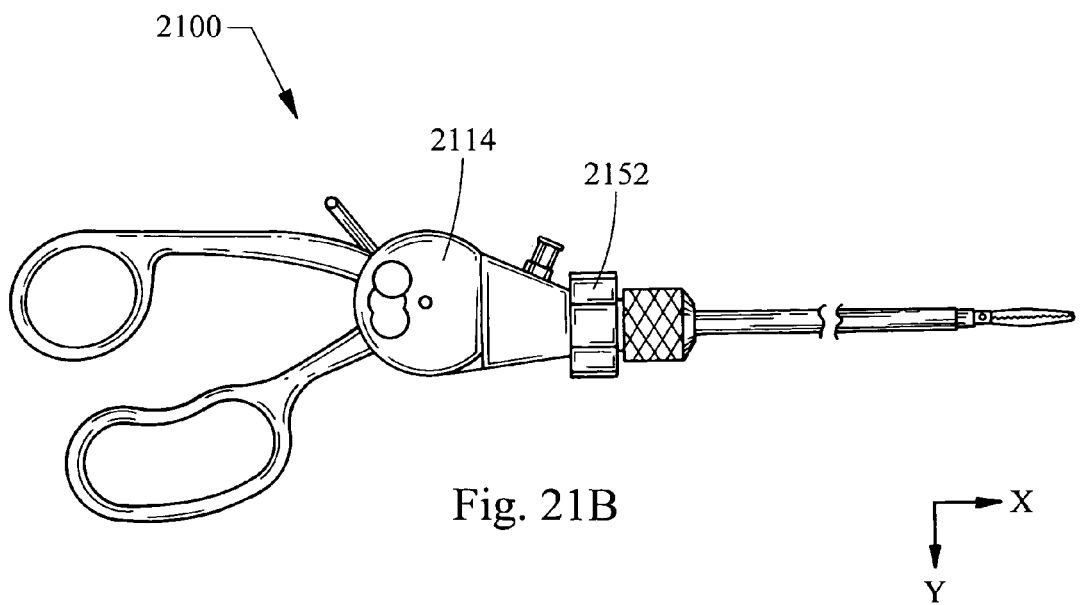
FIG. 21B is a representative front view of FIG. 22A.

Referring to FIGS. 21A and 21B, an alternative embodiment of the present invention shows a laparoscopic instrument 2100 that includes a housing 2114 and a hinge 2152. The hinge 2152 pivots around a Y-axis of the laparoscopic instrument 2100. Specifically, the hinge 2152 pivots around a hinge pin 2152 with respect to the housing 2114. Slots in the housing 2014 and 2114, respectively, and respective drums will enable the exposed part of each respective shaft and ball to travel into each respective drum.

Figure 22A:
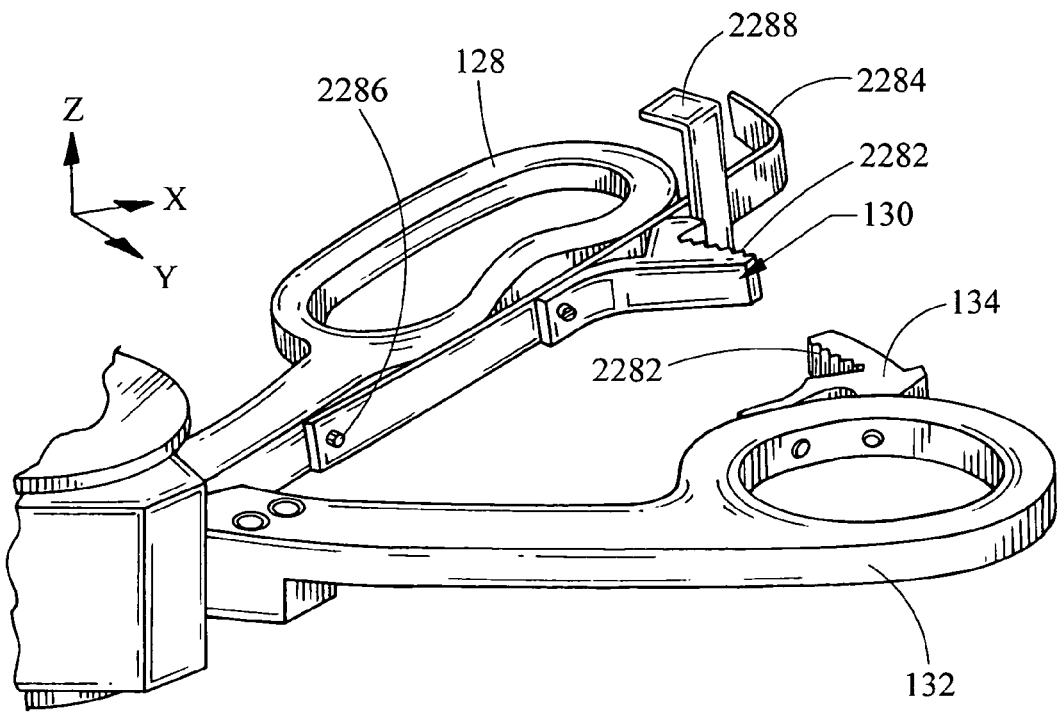
FIG. 22A is a perspective view of a pair of handles of the laparoscopic instrument of FIGS. 1A and 1B in an open aligned position.

Referring to FIGS. 22A-23B, the locking of the trigger handle 128 with respect to the fixing handle 132 will be described in more detail. In FIG. 22A, the handles 128, 132 are in an open and aligned position relative to one another. In the open position there is no contact between the latching mechanism 130 of the trigger handle 128 and the locking part 134 of the fixing handle 132. The latching mechanism 130 and the locking part 134 include a plurality of corresponding teeth 2282 that are biased so as to lock the handles 128, 132 to each other, as described in more detail below in reference to FIG. 22B.

The trigger handle 128 further includes a latching lever 2284, which is pivotally connected to the trigger handle 128 at a pivoting point 2286, and a lever limiter 2288. The lever limiter 2288 limits the rotational movement of the latching lever 2284 to a distance that is sufficient for disengaging engaged ones of the teeth 2282. A reason for limiting the rotational movement of the latching lever 2284 is to prevent the latching lever 2284 from interfering with the operation of the laparoscopic instrument 100. The latching mechanism 130 is mounted on the latching lever 2284 such that the latching mechanism 130 moves whenever the latching lever 2284 is moved. The aligned position shows the latching lever 2284 parallel to the fixing handle 132 in the X-Y plane.

Figure 22B:
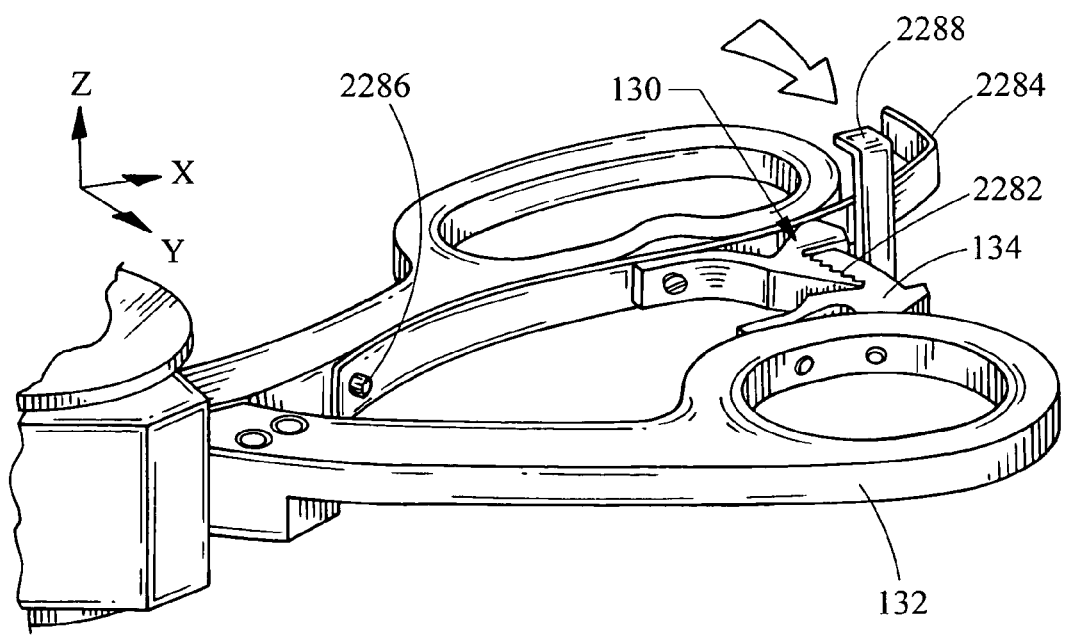
FIG. 22B is a perspective view of the pair of handles of FIG. 22A in a locked position.

In FIG. 22B, the handles 128, 132 are shown in a locked position, and the handles 128, 132 are correspondingly in a closed and aligned position. The latching mechanism 130 and the locking part 134 are interlocked via the plurality of corresponding teeth 2282, which are included in each of the latching mechanism 130 and the locking part 134. To lock the handles 128, 132, at least one of the handles 128, 132 is rotated around the Z-axis toward the other one of the handles 128, 132. For example, the trigger handle 128 is rotated in a clockwise direction toward the fixing handle 132. Corresponding ones of the teeth 2282 are engaged via frictional forces to prevent movement of the handles 128, 132 toward an open position. The teeth 2282 are biased to encourage movement of the handles 128, 132 toward one another but to resist movement of the handles 128, 132 away from one another. The ability to lock the handles 128, 132 during surgery advantageously frees the surgeon's hand to carry out other tasks, while leaving the instrument 100 inside the patient's body. It further permits the surgeon to relax the hand gripping the instrument 100 to minimize hand fatigue that can be caused by prolonged grasping and manipulation of the handles 128, 132. Still further, without locking handles, if the surgeon's hand that is grasping the handles 128, 132 were to momentarily relax or lose its grip, the tool 176 may slip or dislodge from a desired position inside the patient's body cavity. When the handles 128, 132 are in the locked position, the tool 176 can be reliably maintained inside the patient. With the handles locked, the surgeon may also rotate them together in accordance with the present invention to a better position without disturbing the position of the tool 176 inside the body cavity.

Figure 23A:
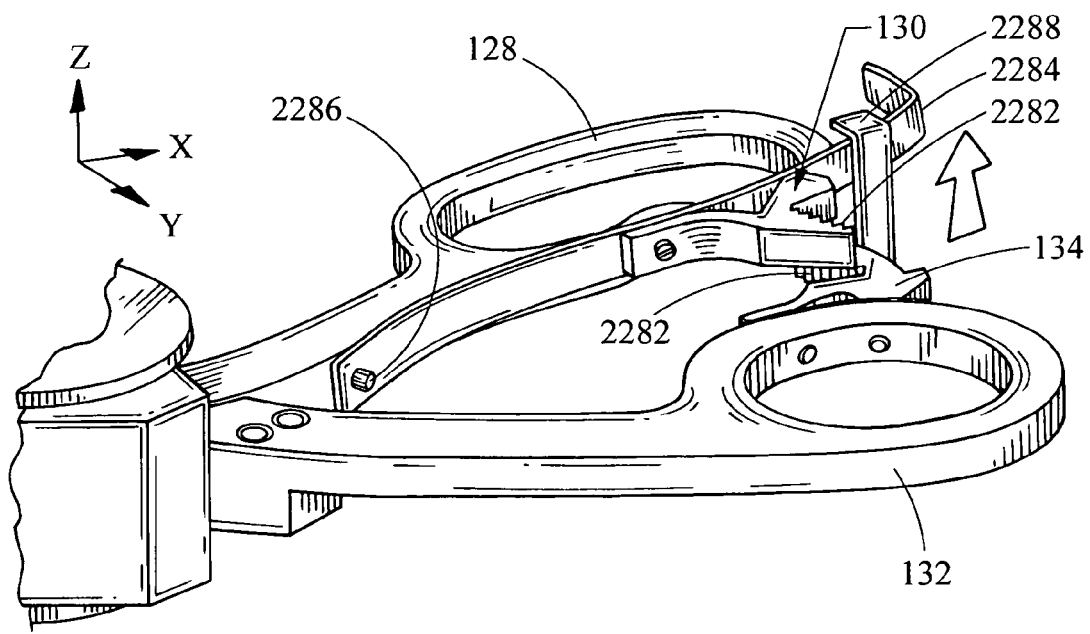
FIG. 23A is a perspective view of the pair of handles of FIG. 22A in a closed offset position.

In FIG. 23A, the handles 128, 132 are shown in a closed and offset position. The handles 128, 132 are fixed with respect to the Z-axis as the latching lever 2284 is urged in the Z-axis direction to unlock the latching mechanism 130 from the locking part 134. When the latching mechanism 130 is moved in the Z-axis direction away from the locking part 134, via movement of the latching lever 2284, engaged ones of the teeth 2282 disengage, causing the trigger handle 128 to unlock from the fixing handle 132.

Figure 23B:
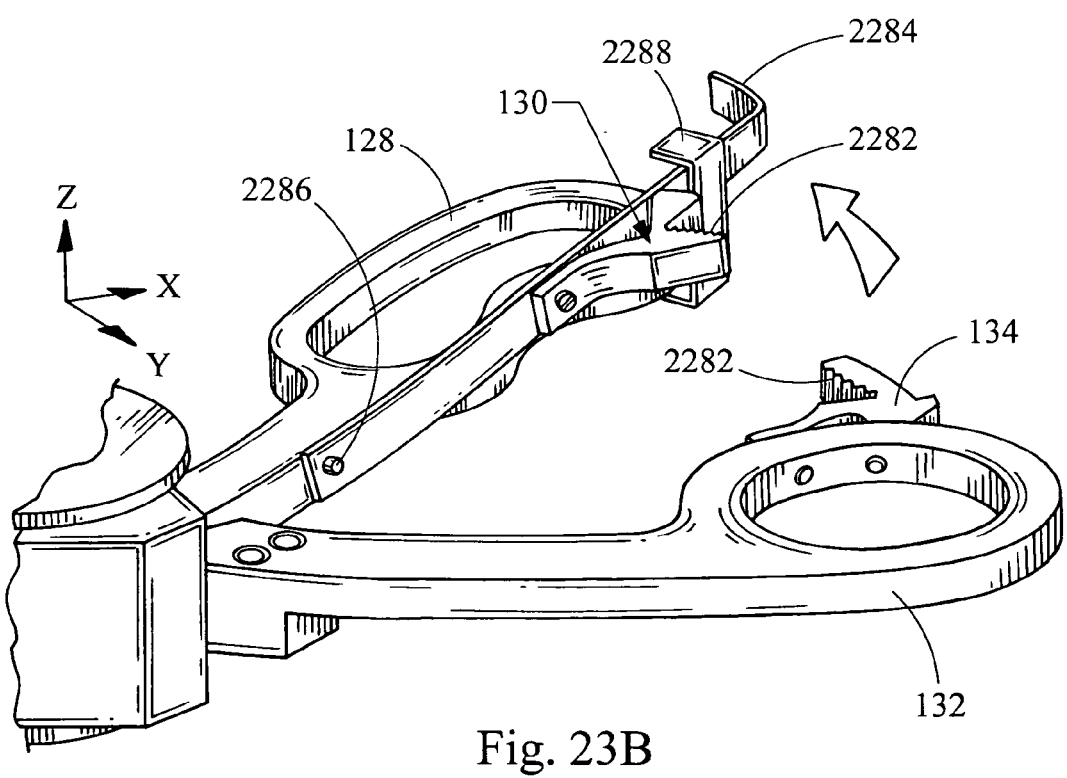
FIG. 23B is a perspective view of the pair of handles of FIG. 22A in an open offset position.

In FIG. 23B, the handles 128, 132 are shown in an open and offset position. After the trigger handle 128 is moved in the Z-axis direction (as shown in FIG. 23A) away from the fixing handle 132, the trigger handle 128 is rotated in a counter-clockwise direction around the Z-axis. To position the latching lever 2284 in the initial open and aligned position of FIG.

22A, the latching lever 2284 must be urged in the Z-axis direction toward the trigger handle 128 in order to position the latching lever 2284 in the same X-Y plane as the fixing handle 132. Now, the trigger handle 128 is ready to be locked relative to the fixing handle 132.

Preferably, the latching lever 2284 is positioned to be manipulatable by the surgeon with a single finger, such as with the pinky finger of the hand grasping the handles 128, 132. In this respect, the surgeon is not required to remove the hand from the handles 128, 132 in order to lock or unlock them. In operation, the surgeon simply moves the latching lever 2284 with the pinky finger, which is typically not positioned within the handle 128 as are the ring and middle fingers.

At least some of the parts described above in reference to FIGS. 1A-23B are injection-molded parts, which are precision molded with hot-oil or water molds using high-strength, graphite-, glass-, or carbon-filled plastics such as PEEK™ (polyetheretherketone), Ultem® (polyetherimide), Grivory®, or RADEL® R (polyphenylsulfone). The injection-molded parts include single cavity molds and family molds. For example, some of the molded parts can be cold runner molds.

Although the foregoing embodiments have been described in connection with a laparoscopic instrument 100, the present invention is equally applicable to an arthroscopic instrument.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A laparoscopic instrument, comprising a first handle pivotally rotatable among at least two lockable positions, and further comprising a second handle pivotally rotatable among the at least two lockable positions with the first handle in a first operating mode and further comprising a first drum attached to the first handle and a shaft passing through the first drum, the first drum being rotatable around the shaft to cause the first handle to be pivotally rotatable among the at least two lockable positions, and a second drum attached to the second handle, the shaft passing through the second drum, the second drum being rotatable around the shaft to cause the second handle to be pivotally rotatable among the at least two lockable positions, wherein said shaft comprises protrusions, wherein said shaft is selectively positionable in at least two operating modes via movement in an axial direction in which, in a first mode position said shaft engages said first drum without engaging said second drum and in a second mode position said shaft engages both said first drum and said second drum.

2. The laparoscopic instrument of claim 1, further comprising:
a tool drum coupled to the second drum in said first operating mode and adapted to be disengaged from the second drum in the second operating mode;
said shaft passing through the first drum, the second drum, and the tool drum wherein the first drum, the second drum, and the tool drum are each rotatable about a central axis of the shaft.

3. The laparoscopic instrument of claim 2, wherein the protrusions on the shaft are disposed along a length of the shaft and positioned to lock together at least two of the first drum, the second drum, and the tool drum while the first handle is rotated among the at least two lockable positions.

4. The laparoscopic instrument of claim 1 further comprising:
a housing;
said shaft passing through a portion of the housing,
a push-button adapted to axially displace the shaft for moving the shaft between the first position and the second position, the second position corresponding to a second operating mode in which the first handle is allowed to pivot between the at least two lockable positions, the first position corresponding to a first operating mode in which the first handle is fixed with respect to the housing in one of the at least two lockable positions.

5. The laparoscopic instrument of claim 4, wherein the first handle is movable between the at least two lockable positions when the shaft is in the second position.

6. The laparoscopic instrument of claim 1 further comprising:
a tool drum, the shaft passing through the tool drum; and
a tool having a coupling end and a tool end, the coupling end being removably connected to the tool drum in any of the at least two lockable positions.

7. The laparoscopic instrument of claim 6, wherein the tool drum is coupled to the second drum when the first handle is in either of the at least two lockable positions.

8. A laparoscopic instrument having a transverse axis along which a tip is disposed, the laparoscopic instrument comprising a first handle pivotally rotatable among at least two lockable positions about an axis substantially orthogonal to the transverse axis, and further comprising a trigger handle pivotally rotatable among the at least two lockable positions with the first handle in a first operating mode and further comprising the trigger handle having a trigger drum attached thereto rotatable about said orthogonal axis, and a tool drum rotatable about said orthogonal axis secured to the trigger drum when the first handle is locked in one of the at least two lockable positions, and a fixing drum attached to the first handle and rotatable about said orthogonal axis, the fixing drum being rotationally secured to the trigger drum when the first handle is not locked in one of the at least two lockable positions, and a shaft, wherein said shaft comprises protrusions adapted to selectively engage, when moved substantially orthogonally to said transverse axis, at least said fixing drum and said trigger drum simultaneously, or said trigger drum and said tool drum simultaneously.

9. The laparoscopic instrument of claim 8, wherein said shaft selectively couples the trigger drum, the tool drum, and the fixing drum to each other, wherein the shaft is movable between a first position and a second position, the tool drum and the trigger drum being rotationally secured with respect to each other in the first position, the trigger drum and the fixing drum being rotationally secured with respect to each other in the second position, the first position corresponding to a mode in which the handle is locked in one of the at least two lockable positions.

* * * * *